(12) United States Patent
Arai et al.

(10) Patent No.: US 6,289,074 B1
(45) Date of Patent: Sep. 11, 2001

(54) X-RAY COMPUTED TOMOGRAPHY METHOD AND SYSTEM

(75) Inventors: Yoshinori Arai, Tokyo; Masakazu Suzuki; Akifumi Tachibana, both of Kyoto, all of (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 09/388,282

(22) Filed: Sep. 1, 1999

(30) Foreign Application Priority Data

Sep. 2, 1998 (JP) .................................................. 10-265667
Sep. 28, 1998 (JP) .................................................. 10-291416

(51) Int. Cl.[7] ...................................................... A61B 6/03
(52) U.S. Cl. .................................................. 378/4; 378/38
(58) Field of Search .................................. 378/4, 20, 38, 378/39

(56) References Cited

U.S. PATENT DOCUMENTS 5,214,686 * 5/1993 Webber .................................. 378/38
5,511,106 * 4/1996 Doebert et al. ........................ 378/146
6,018,563 * 1/2000 Arai et al. ............................... 378/39
6,118,842 * 9/2000 Arai et al. ............................... 378/39

* cited by examiner

*Primary Examiner*—David V. Bruce
(74) *Attorney, Agent, or Firm*—Koda & Androlia

(57) ABSTRACT

An X-ray computed tomography (CT) method of producing sectional images and panoramic images while reducing the exposure dose and time. The method includes producing an X-ray projection image on a two-demensional X-ray image sensor by turning a rotary arm within a scope of angle according to the projection conditions, while locally radiating conical X-ray beams, with a small width in the rotating direction of the beams, with the rotating center of the rotary arm fixed at the center position of the region to be X-rayed and the X-ray projection images are processed using specific equation as previously prepared by a computer to extract image information, and thereby to produce a sectional image of the local region of the object to be examined.

24 Claims, 34 Drawing Sheets

*Fig.17(a)*  *Fig.17(b)* conditional functions of conventional X-ray CT $X = x\cos\theta + y\sin\theta,\ Y = -x\sin\theta + y\cos\theta$     ··· coorinate conversion formula $$p(X,\theta) = \int_{-\infty}^{\infty} f(x,y)\,dY$$     ··· formula 1

$$q(X,\theta) = \frac{1}{2}\int_{-\infty}^{\infty} p(X',\theta) h(X-X')\,dX'$$     ··· formula 2

$$f(x,y) = \frac{1}{2\pi}\int_{0}^{2\pi} q(x,\theta)\,d\theta$$     ··· formula 3

$$f(x,y) = \frac{1}{2\pi}\int_{0}^{2\pi} \frac{1}{2}\int_{-\infty}^{\infty} p(X',\theta) h(X-X')\,dX'\,d\theta$$     ··· formula 4

*Fig.32* conditional functions of X-ray CT (beam width = 2r)

if $|X| \leq r$  $rect_s(X)=1$  else $|X|>r$  $rect_s(X)=0$
if $|X| \leq r$  $rect_n(X)=0$  else $|X|>r$  $rect_n(X)=1$      ··· formula 5
$rect_s(X)+rect_n(X)=1$ $$q(X,\theta)=\frac{1}{2}\int_{-\infty}^{\infty}\{rect_s(X')+rect_n(X')\}p(X',\theta)h(X-X')dX' \quad \text{··· formula 6}$$

$$=\frac{1}{2}\int_{-\infty}^{\infty}rect_s(X')p(X',\theta)h(X-X')dX'+\frac{1}{2}\int_{-\infty}^{\infty}rect_n(X')p(X',\theta)h(X-X')dX'$$

··· formula 6-1

$$=q_s(X,\theta)+q_n(X,\theta) \quad \text{··· formula 7}$$

$$f(x,y)=\frac{1}{2\pi}\int_0^{2\pi}\{q_s(X,\theta)+q_n(X,\theta)\}d\theta$$

$f(x,y)=f_s(x,y)+f_n(x,y)$ $f_s(x,y)=f(x,y)-f_n(x,y)$                     ··· formula 8 wherein  $r^2 \geq x^2+y^2$

*Fig.33* conditional funcions of X-ray CT
for producing panorama image if $|X| \leq r$  $rect_s(X)=1$  else $|X|>r$  $rect_s(X)=0$
if $|X| \leq r$  $rect_n(X)=0$  else $|X|>r$  $rect_n(X)=1$     ··· formula 9
$rect_s(X)+rect_n(X)=1$ $$q(X,\theta)=\frac{1}{2}\int_{-\infty}^{\infty}\{rect_s(X')+rect_n(X')\}p(X',\theta)h(X-X')dX' \quad \text{··· formula 10}$$

$$=\frac{1}{2}\int_{-\infty}^{\infty}rect_s(X')p(X',\theta)h(X-X')dX'+\frac{1}{2}\int_{-\infty}^{\infty}rect_n(X')p(X',\theta)h(X-X')dX'$$

$=q_s(X,\theta)+q_n(X,\theta)$ $=q_s(X,\theta)$    $\because q_n(X,\theta)=0$     ··· formula 11

$$f_s(x,y)=\frac{1}{\psi(x,y)-\phi(x,y)}\int_{\phi(x,y)}^{\psi(x,y)}q_s(X,\theta)d\theta \quad \text{··· formula 12}$$

*Fig.34*

X-RAY COMPUTED TOMOGRAPHY METHOD AND SYSTEM

BACKGROUND OF THE INVENTION

1. Field of the Invention

The present invention relates to an X-ray computed tomography (CT) method and system for producing sectional images of local region and panoramic images of an object by radiating specific conical X-ray beam to the object to be examined.

2. Description of the Prior Art

A method of obtaining a sectional image known as X-ray computer tomography (CT) has been widely used in medical practice as for diagnosis. This method involves radiating X-rays on the object from all around, followed by analyzing three-dimensional absorption coefficient distribution information on the X-rayed object from the projection data by the Radon theory as widely known, thereby obtaining a sectional image of object.

The prior art X-ray CT is a technique in which a fan-shaped X-ray beam relatively wide in the direction of rotation and thin is radiated on the object from around at a depth and this is repeated at different depths.

Accordingly, in the event that only a part inside the object is to be put to tomography examination, the fan-shaped wide X-ray beam is radiated over the whole object to obtain an absorption coefficient distribution information from which the coefficient distribution information on that part or region is taken out for analysis. That is, the object is exposed to a substantial dose of the X-ray beam.

In addition, it takes long to radiograph and analyze the test data. In the light of high dose of radiation, the CT examination is limited to some once a year.

In the prior art panoramic X-ray system, the X-ray beam is scanned over the dental arch from behind roughly crosswise in relation to the dental arch. The rotary arm is so designed that the X-ray generator is moved continually around three different centers a, b and c in the front tooth area of the dental arch, on the right and left of the molar tooth area as shown in FIGS. 24(*a*) to (*c*). That requires a complicated mechanism and control of the rotary arm (not shown) to rotate the X-ray generator 101.

FIG. 25 shows loci of the rotary arm of another prior art panoramic X-ray system during the X-ray examination. The letter Lo designates the axis of symmetry and is the median line of the axial symmetry of a dental arch. The letter L is the X-ray beam bundle roughly perpendicular to the radiation area of the dental arch. The letter La is an envelope line formed by the bundle L of the X-ray beams. In this case, too, the rotary arm has to be so moved as to form an envelope line as shown in the figure. That makes moving mechanism and control complicated.

SUMMARY OF THE INVENTION

The present invention has been developed to solve those problems of the prior art X-ray CT technique.

Therefore, it is an object of the present invention to provide an X-ray CT method that substantially shortens the time required for tomography as compared with the prior art X-ray CT and which greatly reduces the exposure dose of X-ray radiation to the object and permits size reduction of the X-ray system and to provide an X-ray system for the method.

According to the X-ray method of the present invention, since the rotary arm is rotated with the center of the rotary arm fixed to irradiate the conical X-ray beam only on the local region of the object to be examined, the exposure dose of radiation is remarkably reduced from ½ to ¹⁄₁₀₀ that of the prior art X-ray CT examination.

And since the image information is obtained by analyzing absorption coefficient distribution information, the method of the present invention has no problem of being adversely affected by bones or the like of the object. And therefore, it is possible to reduce the whole size of the system. In addition, it may be also possible to design such a vertical-type X-ray CT system as can rotate and irradiate the X-ray in the horizontal direction with the patient in a standing or sitting position. That is, the present invention can provide a small-size X-ray CT system suitable for use in such dentists as to have only a limited floor space.

It is another object of the present invention to provide an X-ray CT method that can produce panoramic images just by putting the rotary arm in a circular motion unlike the prior art panoramic image X-ray method in which the rotary arm had to be rotated while swing back and forth, right and left the center thereof and to provide an system for the method.

It is still another object of the present invention to provide an X-ray method that can produce panoramic images by substantially reducing the exposure dose of radiation to the object to be examined and to provide an X-ray system for the method.

After intensive researches, the inventors succeeded in developing this X-ray CT method and the system. According to the present invention, desired local radiated surface images and panoramic images can be obtained just by radiating the conical X-ray beam—row in the rotating direction and having a certain thickness in the vertical direction—as if wrapping such parts as the intended local region of the object and a specific region about in the center of the dental arch. The method and system according to the present invention is suitable for X-ray examination of such local regions as the denture and maxillofacial areas and nondestructive examination of small structures.

The X-ray CT method according to the present invention involves locally radiating the conical X-ray beam to only the local region of the object by rotating the rotary arm with the X-ray generator and the two-dimensional X-ray image sensor disposed opposed to each other. This radiographing is performed with the X-ray generator radiating the conical X-ray beam on only the local region to X-ray and with the rotary arm fixed with its rotation center on the central position of the local region to radiograph.

The rotary arm does not always have to be rotated around the local region but the circle to be covered may be from some 5 degrees to the full circle, that is, 360 degrees as necessary. This may be called an improvement on the prior art the present inventors disclosed in Japanese patent application laid on unexamined under No. H10-225455.

The prior art was a panoramic tomography and local CT technique and its feature included the fixing of the rotation center and partial CT of the local region. But that did not describe specifically the local radiation or the feature of the present invention. Also, the prior art called for the full circumferential radiation as the conventional CT systems.

By contrast, the present invention is characterized in that local radiation is specifically described and the scope to be covered by radiation is not limited to the full circle of 360 degrees but may be selected depending on the needs.

After extensive study, the inventors found that radiation of the conical X-ray beam in a scope of angle depending on the kind of required CT images could produce coefficient distribution information from which desired images could be obtained. The present invention is based on that discovery.

According to the present invention, radiation covering only 5 to 90 degrees will do in the radiographing in the direction perpendicular to the denture of the front teeth. Also, to produce panoramic images of the whole jaw of the dental arch, radiation should cover just the angular scope perpendicular to the dental arch, that is, about 180 degrees. This idea has been further developed into the X-ray CT method to obtain panoramic images of the dental arch.

In the present invention, furthermore, X-ray projection images produced on the two-dimensional image sensor is processed and reconstructed by a computer. That is, if an X-ray projection image is backprojected and put to a specific arithmetic processing, a three-dimensional absorption coefficient distribution information on the inside of the X-rayed local region can be taken out as an image information. If a specific object section is designated or a specific body section is set up before hand, its sectional image can be produced.

The radiographic method of the present invention is based on this idea. While projection data can always be obtained on the local region exposed to local radiation of the conical X-ray beam, the other part of the object surrounding the local region has less effect on projection data than the local region because the conical X-ray beam passes through it transiently as the arm rotates. In backprojection, therefore, the effect on other than the local region can be largely ignored. In case much difference is observed in coefficient distribution information on the object between the local region to be X-rayed and the surrounding parts, that is, in case there are teeth, bone implant or the like in the local region, the sectional image obtained is good enough in contrast for examination of the form of those objects. Therefore, the projection image obtained by local radiation of the conical X-ray beam only on the local region can be well used for diagnosis in practice after being analyzed.

The present invention also includes an X-ray CT method in which the analysis technique to practice the X-ray CT method is shown in specific operation expressions.

That analysis technique is to work out approximately the X-ray absorption coefficient distribution. That is, the backprojection data of the projection data is integrated only on the local region exposed to local radiation by the widely used convolution method. Two-dimensional absorption coefficient distribution is worked out into images. Practical three-dimensional distribution information can be calculated by adding two-dimensional distributions. This analysis technique will be described later.

Also proposed is an X-ray CT method used to produce panoramic images of the dental arch.

This method is to produce panoramic images of the dental arch from three-dimensional absorption coefficient distribution information this way. A virtual local region is worked out that is always exposed to a conical X-ray beam in specific loci that was needed to produce panoramic images in the prior art. With the rotation center of the conical X-ray beam fixed at the center position of that virtual local region, the conical X-ray beam is locally radiated in such a way to cover only the virtual local region. Only partial X-ray projection images by the conical X-ray beam is taken out from the X-ray projection images of the dental arch obtained. On the basis of the partial X-ray projection images, a backprojection is conducted to obtain three-dimensional absorption coefficient distribution information of the dental arch. From the three-dimensional absorption coefficient distribution information is produced the panoramic images of the dental arch. That way, the same panoramic images of the dental arch as that by the conical X-ray beam in the prior art can be obtained by the X-ray CT method.

The principle of that idea is a further development to an X-ray CT method from the X-ray CT requiring radiation of the conical X-ray beam to the whole of the object. If a virtual local region is selected that way, the radiation of the conical X-ray beam is limited to a specific scope of angle. But if care is taken to pick out only the partial X-ray projection images exposed to the conical X-ray beam at the scope of angle, then image data can be obtained that are good enough for panoramic images. That is, absorption coefficient distribution is obtained from the partial X-ray projection images to produce panoramic images.

The virtual local region to obtain panoramic images of the dental arch are often located in or near the center of the dental arch or at a suitable point between the dental arch and the cervical vertebra area on the axis of symmetry of the dental arch. That point is advantageous in that few obstacles are present there.

The X-ray CT method can produce panoramic images without the rotary arm following complicate loci to form an envelopment (as in FIG. 25) as in the prior art. In the present invention, radiographing is performed with the center of rotation fixed at a specific point. Therefore, the system for that can be configured almost the same way.

The present invention also proposes a method of producing panoramic images of the dental arch by taking out three-dimensional absorption coefficient distribution information of the dental arch as image information this way. When a specific width of the conical X-ray beam is radiated on the local region by rotating the rotary arm with the X-ray generator and the two-dimensional image sensor faced to each other, the rotation center of the rotary arm is fixed at such a center position of the virtual local region as includes the loci of the conical X-ray beam needed to obtain panoramic images of the dental arch, or part of the object. This rotary arm is rotated only for the scope of angle for the radiographing requirements to radiate the conical X-ray beam from the X-ray generator to the virtual local region only. Thus are produced the X-ray projection images one after another on the two-dimensional image sensor. From the X-ray projection images produced one after another on the two-dimensional image sensor is picked out the partial X-ray projection images only that are produced by the conical X-ray beam roughly perpendicular to the dental arch. The picked out partial X-ray projection images are arithmetically processed to extract the three-dimensional absorption coefficient distribution information of the dental arch as image information to form panoramic images of the dental arch.

It is understood that the conical X-ray beam is a conical X-ray beam that is locally radiated to produce panoramic images of the dental arch and which is roughly perpendicular to the dental arch. The reason why that conical X-ray beam alone is extracted is this. The partial X-ray projection images by the conical X-ray beam contain projection data most suitable for formation of panoramic images of the dental arch, that is, projection data in which teeth are less overlapped.

This radiographing method is based on the aforethe the local X-ray methods. In this method, however, to be always exposed to the conical X-ray beam are not only the dental arch or the object for producing panoramic images but also an area which is always radiated by rotating the conical X-ray beam with a specific width with a specific point roughly in the center of the dental arch, preferably inside of the dental arch, as center—the area called the virtual local region. That is, the feature of this method is that the dental arch or the region to be X-rayed to produce images is the virtual local region which is always exposed to local radiation of the conical X-ray beam.

While the projection data is small that can be obtained with the conical X-ray beam locally radiated to the dental arch to produce panoramic images, panoramic images clear enough for use in practice can be obtained. That is because the virtual local region selected is the area about in the center of the dental arch where there are less obstacles and, in addition, the partial X-ray projection images only by the conical X-ray beam are picked out.

The rotation center of the rotary arm is fixed at a specific point roughly in the center of the dental arch, preferably inside the dental arch. The exact point of the rotation center of the rotary arm is selected in consideration of the pojecting conditions as in the orthogonal projection panoramic radiographing and standard panoramic radiographing and radiation exposure dose.

In orthogonal projection panoramic radiographing, the bundle of X-ray beams is radiated on the dental arch in a direction about perpendicular to the dental arch. That is, a specific width of the conical X-ray beam is locally radiated in such a way that the inscribed circle on the envelope formed by the loci of the rotary arm moved in practicing the conventional radiographing method is the virtual local region.

Furthermore, the present invention provides an X-ray CT method in which concrete operational expressions represent an analysis technique for carrying out the X-ray CT method used to produce panoramic images.

The analysis technique is different in this way. When X-ray absorption coefficient distribution is worked out from the backprojection data of the dental arch with the width of the conical X-ray beam in the rotating direction as 2r, the following two radiation angles are used: the radiation angle $\phi$ (x, y) of the conical X-ray beam when the conical X-ray beam begins to radiate that point and the radiation angle $\phi$ (x, y) when the radiation of that point ends. In addition, the integration scope is limited to that range. The principle of this analysis technique will be described later.

Also, the present invention calls for selective radiation of the conical X-ray beam by moving a slit before the X-ray generator in the X-ray scanning direction during projection this way. Out of the conical X-ray beam radiated on the dental arch by the X-ray generator, the aforesaid conical X-ray beam only is selectively shed synchronizing with the rotation of the rotary arm during projection, thus forming the aforesaid X-ray projection images of the dental arch on the two-dimensional image sensor. That way, the conical X-ray beam is selectively radiated by moving a slit before the X-ray generator in the X-ray scanning direction during projection.

That reduces the X-ray exposure dose of the object by the difference resulted from switching from the conical X-ray beam to the conical X-ray beam.

By the way, there will be described the X-ray CT systems to practice the X-ray CT methods using a conical X-ray beam.

The X-ray CT system comprises: X-raying means having a rotary arm with an X-ray generator and a two-dimensional X-ray image sensor faced to each other; X-ray beam width restriction means for restricting the width at least in the scanning direction of the conical X-ray beam radiated from the X-ray generator; rotary arm drive control means that makes it possible to move and set up the rotation center of the rotary arm before the X-raying or to move and set up the object before the X-raying and rotates the rotary arm with the rotation center of the rotary arm fixed during X-ray projection; and an image processing unit for arithmetically processing the X-ray projection data and taking out a three-dimensional absorption coefficient distribution information—on the inside of the object through which the X-ray is passed—as image information. The rotary arm does not necessarily have to be rotated all around the local region but may be half or 180 degrees rotated.

The image processing unit reconstructs images of the X-ray projection data—obtained by X-raying the local region or the partial X-ray projection images of the object— by a known arithmetic operation such as the backprojection. The projection data produced on the two-dimensional image sensor by the rotary arm one after another are inputted into the image processing unit for image processing. And the three-dimensional absorption coefficient distribution information on the inside of the object can be taken out as an image information. Therefore, a specific object section is designated or set up beforehand, then the image on that section can be produced.

Furthermore, the present invention provides an X-ray CT system to practice the X-ray CT method used to produce panoramic images.

The X-ray CT system proposed here comprising: X-raying means having a rotary arm with an X-ray generator and a two-dimensional X-ray image sensor faced to each other; X-ray beam width restriction means for restricting the width at least in the scanning direction of a conical X-ray beam radiated from the X-ray generator; rotary arm drive control means that makes it possible to move and set up the rotation center of the rotary arm before X-raying or to move and set up the object before X-raying and rotates the rotary arm with the rotation center of the rotary arm fixed during projection; and an image processing unit for arithmetically processing the X-ray projection data and taking out a three-dimensional absorption coefficient distribution information—on the inside of the object through which the X-ray is passed—as image information, wherein the three-dimensional absorption coefficient distribution information on the dental arch is picked out as an image information this way. The rotation center of the rotary arm is fixed at such a center position of the virtual local region as includes the loci of the conical X-ray beam needed to obtain panoramic images of the dental arch, or part of the object. The rotary arm is rotated only for the scope of angle for the radiographing requirements to radiate the conical X-ray beam from the X-ray generator to the virtual local region only. Thus are produced the X-ray projection images one after another on the two-dimensional image sensor. From the X-ray projection images produced one after another on the two-dimensional image sensor is picked out the partial X-ray projection images only that are produced by the conical X-ray beam. The picked out partial X-ray projection images are arithmetically processed to extract the three-dimensional absorption coefficient distribution information of the dental arch as image information to form panoramic images of the dental arch. The scope of angle for the radiographing requirements is between 180° and 240° for the radiographing of the whole jaw.

The X-ray CT system proposed has the X-ray generator provided with a radiation control slit for selectively radiating the conical X-ray beam only out of the specific width of the conical X-ray beam by synchronizing with the rotation of the rotary arm. And partial X-ray projection images of the dental arch on the two-dimensional image sensor are produced by the conical X-ray beam radiated through the radiation control slit.

The X-ray CT system has the X-ray generator provided with a radiation control slit for selectively radiating the conical X-ray beam only out of the specific width of the conical X-ray beam by moving the slit before the X-ray generator in the X-ray scanning direction synchronizing with the rotation of the rotary arm during projection. And partial X-ray projection images of the dental arch on the two-dimensional image sensor are produced by the conical X-ray beam radiated through the radiation control slit.

That way, the X-ray exposure dose of the object is reduced by the difference between the conical X-ray beam and the conical X-ray beam.

The X-ray CT system has a selection switch that permits selection between the ordinary X-ray CT mode and another mode to produce panoramic images of the dental arch. That is, one system can produce both ordinary sectional images and panoramic images.

To further illustrate, the proposed X-ray CT system has a selection switch that is set to the local CT mode when sectional images of the local region is to be produced and to the panoramic radiographic mode when panoramic images of the dental arch are to be obtained.

Furthermore, different variations are proposed.

One of them is characterized in that the conical X-ray beam from the X-ray generator is locally radiated to the two-dimensional image sensor horizontally with the axis of rotation of the rotary arm in the vertical direction. In this system, the rotary arm rotates horizontally with the axis of rotation of the rotary arm held vertically. And the conical X-ray beam is radiated locally and horizontally. Therefore, it is possible to reduce the space for installation of the system.

Another variation has a two-dimensional image sensor not longer than 30 cm in length and not longer than 30 cm in width which can detect not smaller than 30 pieces of X-ray projection image data or partial X-ray projection image data. In the ortho X-ray CT method, only the X-ray projection images on the local region alone are needed. In this system, therefore, the two-dimensional image sensor can also be reduced in size. And the amount of the X-ray projection images obtained is decreased. In turn, the processing time is shortened, and the amount of the X-ray projection images that can be detected in a specific time increases. That is, the system can be reduced in size and the radiographing work will be sped up.

Still another variation is that the main frame rotating and holding at least the rotary arm has arm vertical position adjusting means for adjusting and setting the position of the arm in the vertical direction. In this variation, the vertical position of the rotating plane of the rotary arm can be adjusted to the height of the object.

A further variation is provided with means for holding the object and this object holding means is equipped with object horizontal position adjusting means that permits position the object at least in the horizontal direction. The rotation center of the rotary arm has to be adjusted to the center position of the local region or a specific position roughly in center of the dental arch. In this system, instead of moving the rotary arm, the object is moved horizontally by the object holding means which has object horizontal position adjusting means that permits position the object at least in the horizontal direction.

Yet another variation is proposed that has object vertical position adjusting means that can position the object at least in the vertical direction and optical beam radiation means for shedding optical beams to optically specify the rotation center of the rotary arm and the radiation axis of the conical X-ray beam. That is, this system is provided with optical beam radiation means for indicating the horizontal position and vertical position of the rotation center of the rotary arm and if the object holding means is set along with the specifying of the position of the object to the optical beam radiation means, then the position of the object can be put in position to practice the X-ray CT method.

A still further variation is proposed from a different approach. Proposed is so configured that the rotation center of the rotary arm is fixed at the center position of the local region or the center position of the virtual local region this way. A dental articulation model taken from the object is secured to the object holding means, followed by moving a local region or a virtual local region of the object that is to be X-rayed—indicated by the dental articulation model—to the position specified by the optical beam radiation means by the object horizontal position adjusting means or object vertical position adjusting means and then setting the object on the dental articulation model, thereby fixing the rotation center of the rotary arm in the center position of the local region or the center position of the virtual local position. The expression "dental articulation model" as used generally in practice denotes a model copied from the patient's teeth showing the occlusion. The model is prepared for each patient and used for treatment at the dentist's. The expression as used herein has a broader meaning, referring to a model copied from part of the outside form of an object in a specific shape. If this dental articulation model is positioned, it is possible to determine the position of an internal point of the object in a specific shape modeled after. In this system, the positioning is effected not on the outside of the object but with that dental articulation model. That makes it possible to fix the rotation center of the rotary arm at the center position of the local region of the object or at the center position of the virtual local region more accurately.

Still another variation uses a direct driven rotation control motor provided on the rotation center as rotation control means for the rotary arm. The expression "rotation control motor" as used herein refers to a motor that permits free control of the rotating speed and the rotation position.

Direct-driven, the system has no axial vibration. Driven by such a rotation control motor, the rotary arm can be rotated accurately at a desired speed and can be stopped at a desired position, which helps carry out the X-ray CT method efficiently.

Yet a further variation is provided with a hollow in the rotation center of the rotary arm. In this system, the necessary wiring or the like can be led to the X-ray generator and the two-dimensional image sensor can be led through that hollow provided in the rotation center of the rotary arm. That can minimize the interference with the wiring of the rotary arm and adds up the aesthetics of the wiring.

Another variation uses either TFT, MOS, CCD, XII or XICCD as the two-dimensional image sensor. A still further variation is that the standby position of the rotary arm is provided at a such point as not to stand in the way of the object coming in and going out when the object is set up for an X-ray CT session or released after the X-raying. Those systems are convenient in that the rotary arm waits at a standby position that obstructs the object coming in and going out.

BRIEF DESCRIPTION OF THE DRAWINGS

FIG. 17 illustrates one embodiment of MOS used for a two-dimensional X-ray image sensor according to the present invention, FIG. 17(a) is its circuit, FIG. 17(b) is its timing chart.

FIG. 32 shows conditional expressions (formula 1) to (formula 4) used for analyzing the basic principle of an X-ray CT.

FIG. 33 shows conditional expressions (formula 5) to (formula 8) used for analyzing the basic principle of an X-ray CT.

FIG. 34 shows conditional expressions (formula 9) to (formula 12) used for analyzing the basic principle of an X-ray CT for producing a panorama image.

DETAILED DESCRIPTION OF THE INVENTION

The present invention will be described referring to the attached drawings hereinafter wherein the embodiment is described as an X-ray computed tomography which is representatively used as X-ray computed tomography, however, the present invention should not be limited to such an X-ray computed tomography.

Figure 1:
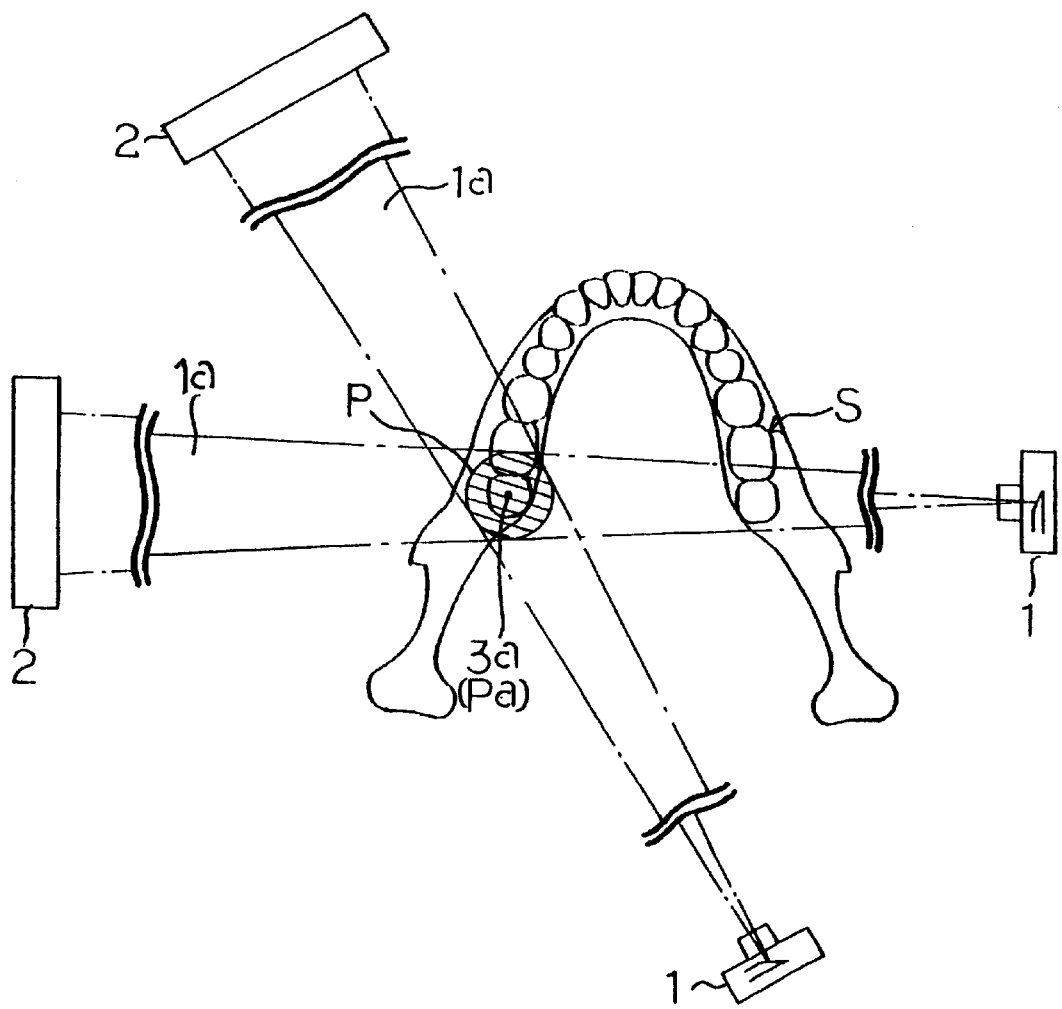
FIG. 1 illustrates a basic principle of an X-ray CT method of the present invention. (when cheek teeth is projected)
Figure 2:
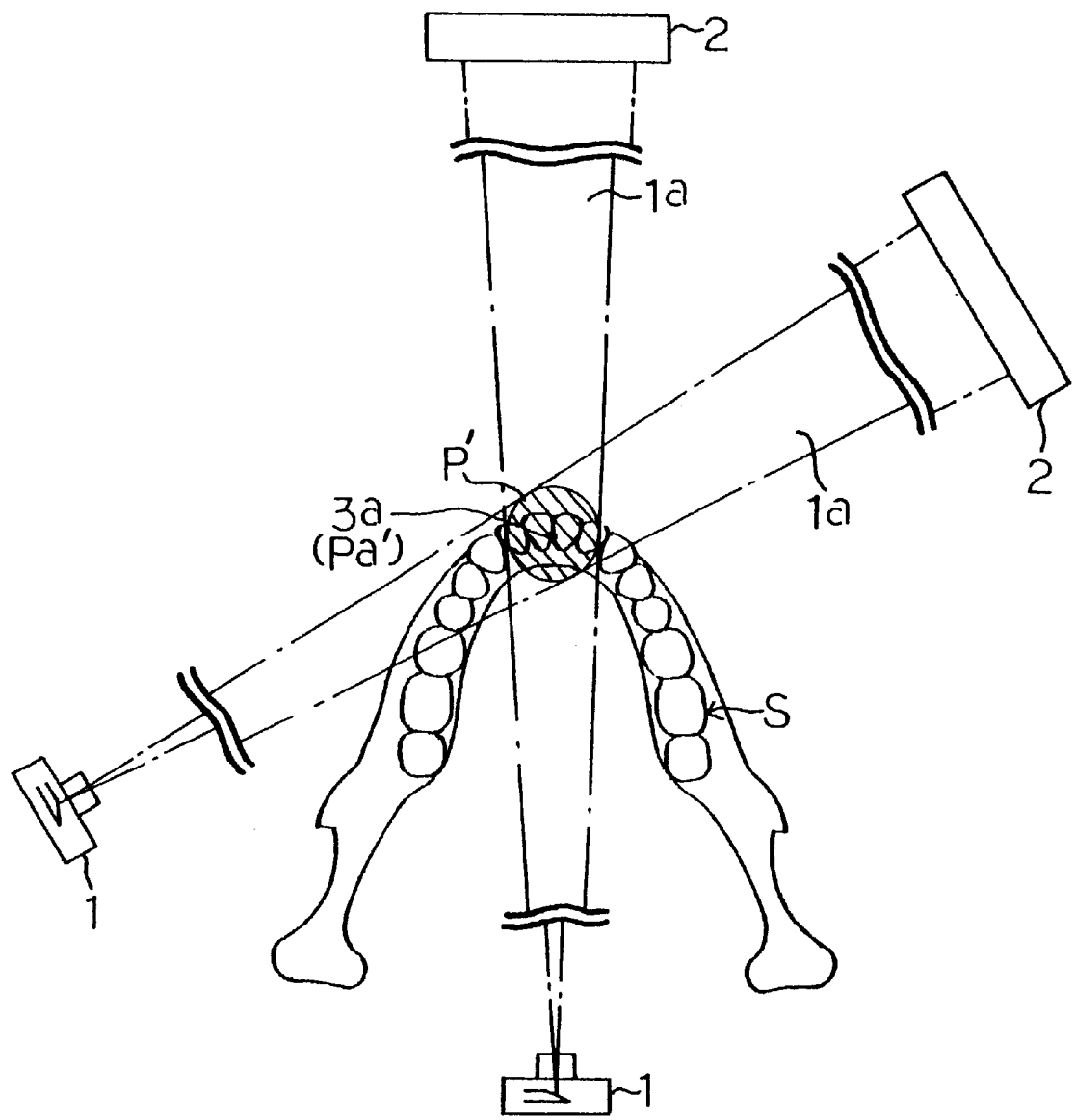
FIG. 2 illustrates a basic principle of another X-ray CT method of the present invention. (when front teeth is projected)

FIG. 1 and FIG. 2 show a basic principle of an X-ray computed tomography (CT) method of the present invention.

In these figures, the reference numeral 1 shows an X-ray generator and 2 shows a two-dimensional image sensor. They are faced to each other and provided for a rotary arm 3 which will be explained referring to FIG. 8 and FIG. 9 hereinafter. The reference characters P and PI show cheek teeth and front teeth, which are local regions to be projected, respectively and S shows a dental arch.

According to the projection method of the present invention, as shown in FIG. 1 and FIG. 2, the rotary arm 3 is rotated at a constant velocity around center positions Pa, Pa' of the local regions P, P' on a center 3a thereof. In this case, the X-ray generator 1 emits a conical X-ray beam 1a having a beam width to include only the local regions P, P'. Therefore, an X-ray projection image of the local regions P, P' having a fixed pace of expansion is sequentially generated at a projection surface 2a of the two-dimensional X-ray image sensor 2.

As a two-dimensional an X-ray image sensor, an X-ray TFT (Thin Film Transistor) sensor, an X-ray MOS (Metal Oxide Semiconductor) sensor, an X-ray II (Image Intensifier) camera, an X-ray amorphous serene sensor, an X-ray CCD (Charge Coupled Device) sensor, and an X-ray CCD sensor (XICCD) with an amplifier are used.

Thus projected X-ray projection image is processed such as a backprojection by a computer and an X-ray absorption coefficient distribution in the local regions P, P' can be taken out as an image information. Therefore, when an optional section of the local regions P, P' is specified or predetermined, the sectional image can be obtained.

The rotary arm 3 is rotated holding the center 3a at the centers Pa, Pa' of the local regions P, P'. In this case, the conical X-ray beam 1a is locally radiated so as to always include only the local regions P, P'. According to the projection condition, at least the local regions P, P' are radiated half cycle, an optional sectional image of the region can be produced.

Figure 3A:
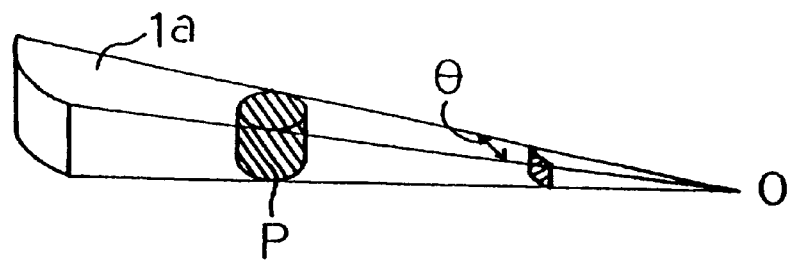
FIG. 3(a) and FIG. 3(b) are explanatory view comparing a conical X-ray beam and a fan shaped X-ray beam.
Figure 3B:
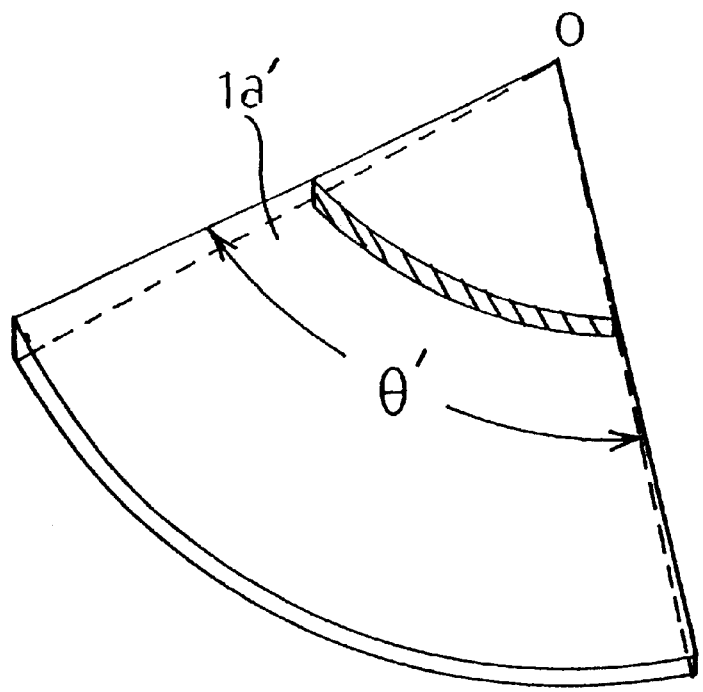

FIG. 3(a) is a detailed view of the conical X-ray beam radiated from the X-ray generator 1 and FIG. 3(b) is a conventional fan shaped X-ray beam 1a'.

The conical X-ray beam 1a has a small angle θ enlarging in a scanning direction and has a fixed thickness vertically comparing to that the conventional fan shaped X-ray beam 1a' has a large angle θ' enlarging in a scanning direction and has small vertical spreading. The conical X-ray beam 1a is a beam bundle which can pass the X-ray out of the whole local region P to be projected at one beam radiation.

The conical X-ray beam 1a can be formed at an optional sectional shape. When the sectional shape is rectangular and the conical X-ray beam 1a is radiated from all the circumference at only one part of an object to be projected (called an object hereinafter), the local region P to which the conical X-ray beam 1a is commonly and locally radiated becomes cylindrical as shown in FIG. 3(a). Therefore, the inside distribution of the X-ray absorption coefficient can be calculated and the sectional image of the optional section inside the cylinder area can be obtained. When the section is made circular and the conical X-ray beam 1a is locally radiated only at a part of the object, the part where the conical X-ray beam 1a is commonly radiated becomes spherical. Therefore, the inside X-ray absorption coefficient distribution can be calculated and the sectional image of the optional section in the sphere can be obtained.

When the X-ray CT method is used for dental care, a two-dimensional X-ray image sensor with 10 cm height and 10 cm width is used. In such a case, the cylinder, namely a local region, becomes 5 cm diameter and 5 cm height.

The rotary angle of the rotary arm 3 can be set accordingly from 5° to 360°. When the arm 3 is rotated at least 5° around the direction vertical to the section to be projected, the sectional image can be produced from the X-ray projection data. On the other hand, the arm 3 should be rotated from 180° to 240° in order to produce all the optional section of the local region P. If it is rotated 360°, the resolution can be made all around. However, pictures from 360° isn't always required.

Then the X-ray CT method for producing a panorama image of a dental arch will be explained hereinafter.

Figure 4:
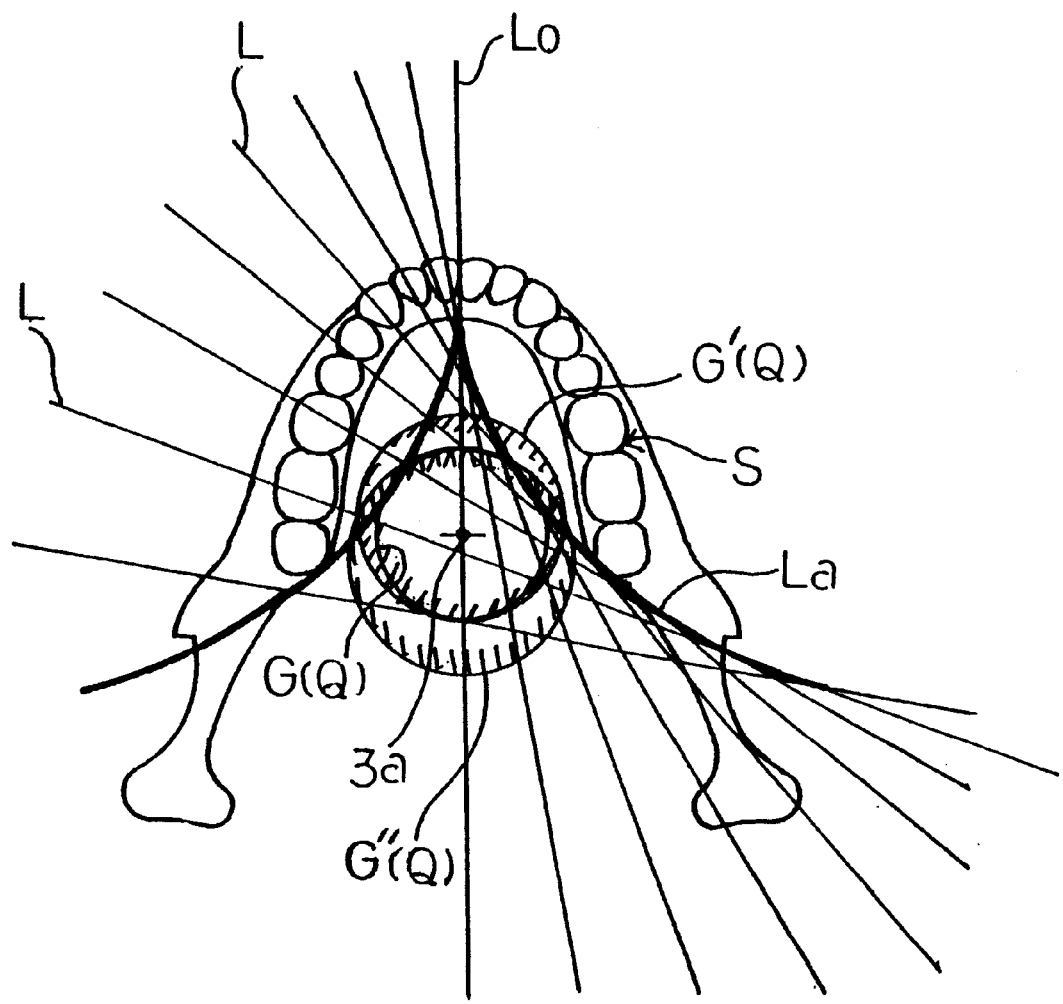
FIG. 4 illustrates a setting position of a center of a rotary arm for executing an X-ray CT method for producing a panorama image of a dental arch.

FIG. 4 explains a setting position of the center 3a of the rotary arm 3 which is set for executing an X-ray CT for producing a panorama image.

In the X-ray CT method for producing a panorama image of the dental arch S according to the present invention, the center 3a of the rotary arm 3 is fixed at a fixed position (preferably inside of the dental arch S) on the axis of symmetry Lo at the center of the dental arch S. And while the arm 3 is rotated at a constant velocity within a rotary angle according to the projection condition, the conical X-ray beam 1a of a fixed width is locally radiated and the X-ray projection image of the dental arch S is obtained.

Generally, when a normal panorama projection is executed, it is required to be the X-ray beam bundle approximately orthogonal for all tooth of the dental arch S. Such an X-ray beam bundle is shown as L in FIG. 4.

Figure 5:
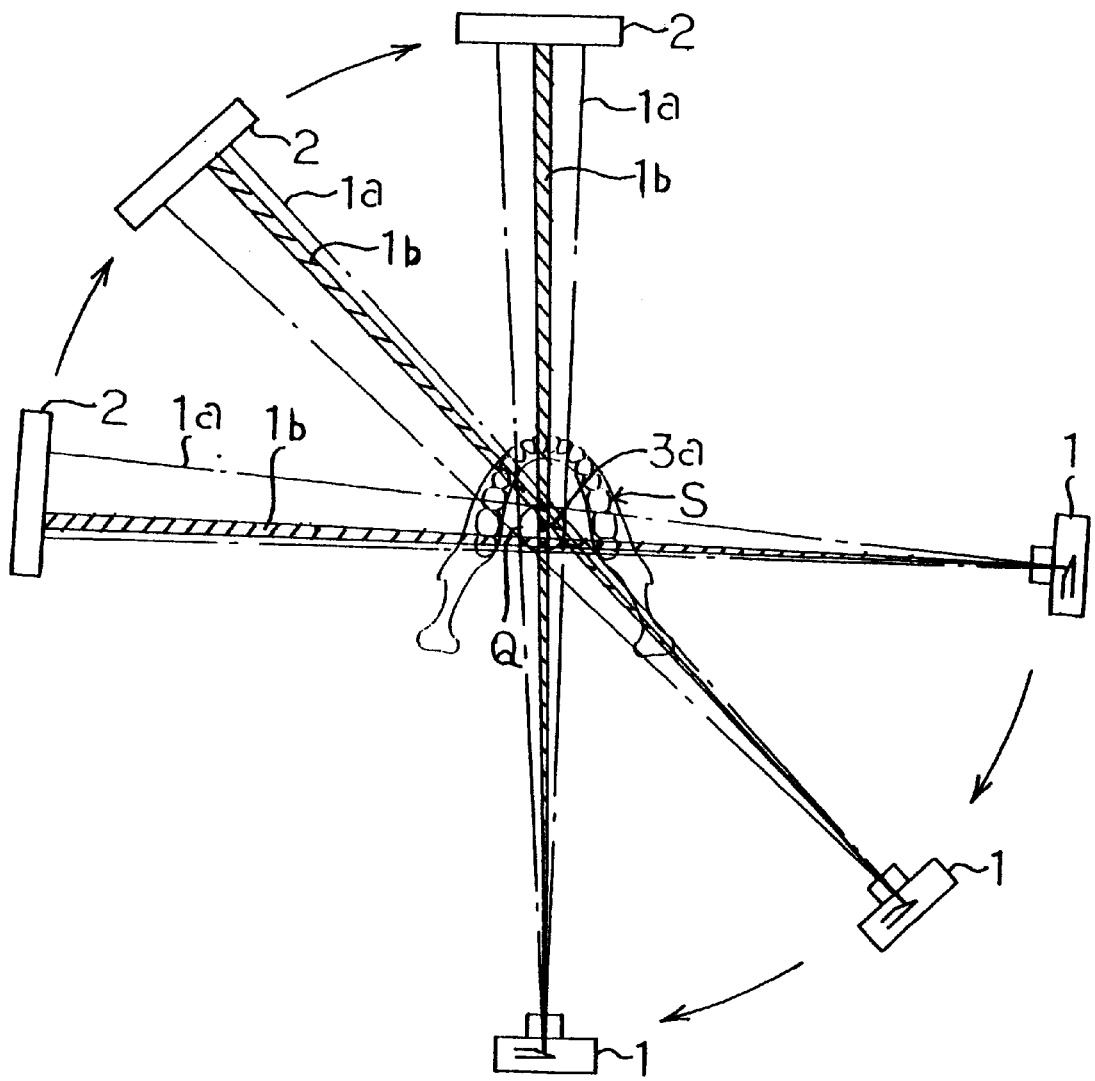
FIG. 5 shows an X-ray CT projection method for producing a panorama image according to the present invention.

When an orthogonal X-ray beam bundle L . . . for all the tooth of the dental arch S is drawn, an envelope curve La of these X-ray beam bundles L . . . is formed. Then an encircle G which touches internally to the envelope curve La is considered, all the X-ray beam bundles L for the dental arch S passes through the encircle G. Therefore, the conical X-ray beam 1a having a fixed width is locally radiated from circumference so as to locally radiate the encircle G, with a center Ga of the encircle G as the center 3a of the rotary arm 3, the conical X-ray beam 1a always include X-ray beam orthogonal to the dental arch S. That is, in this example, the encircle G becomes the above-mentioned virtual local region as shown in FIG. 5 and the region is represented by the reference character Q. The X-ray beam bundle orthogonal to the dental arch S is the above-mentioned conical X-ray beam and is represented by the reference number 1b.

When the conical X-ray beam 1a is locally radiated so as to form the virtual local region Q, the partial X-ray projection image formed by the conical X-ray beam 1b approximately orthogonal to the dental arch S is extracted from the X-ray projection images of the dental arch S sequentially produced on the two-dimensional X-ray image sensor 2. Then a three-dimensional X-ray absorption coefficient distribution information of the dental arch S is taken out as an image information by processing the image and a continuous orthodox projection panorama image of the dental arch S can be produced.

The X-ray CT method of the present invention to produce a panorama image of the dental arch S is based on such a theory. The position of the center 3a of the rotary arm 3 and the width of the conical X-ray beam 1a, namely the position and dimension of the vertical region Q, are properly set according to the mode of the image to be produced finally. In a word, the conical X-ray beam complying with the mode of the image is designed to be included in the conical X-ray beam.

For example, the position of the center 3a of the rotary arm 3 and the width of the conical X-ray beam which are set at projection, namely the virtual local region Q, aren't limited in the encircle G which touches internally to the above-mentioned envelope curve La. They may be a circle including the encircle G shown as G' or G" in FIG. 4. If such a circle is defined as the virtual local region Q, the area center is always positioned on the axis of symmetry Lo inside of the dental arch S.

As a panorama image, it isn't limited to an orthodox projection panorama image and there are a standard panorama image, and a jawbone panorama image. So, a conical X-ray beam isn't necessarily orthogonalized against a dental arch S. Therefore, when a panorama image by such a projection method is produced, the position of the center 3a of the rotary arm 3 on the axis of symmetry Lo of the dental arch S and the width of a conical X-ray beam 1a, namely the virtual local region Q, is required to be positioned so as to include these all conical X-ray beam 1b. One of the example is the abovementioned encircles G', G".

The virtual local region Q for producing the panorama image is decided corresponding to the panorama image to be produced. In view of abatement of an X-ray exposed dose, it goes without saying that the area Q is preferably small.

As shown in FIG. 4, the rotary arm 3 isn't required to be rotated 360° and may be rotated about from 180° to 240° to picture an image. Therefore, an X-ray exposed dose and a projection time can be reduced at the rate of the reduced angle.

Figure 6:
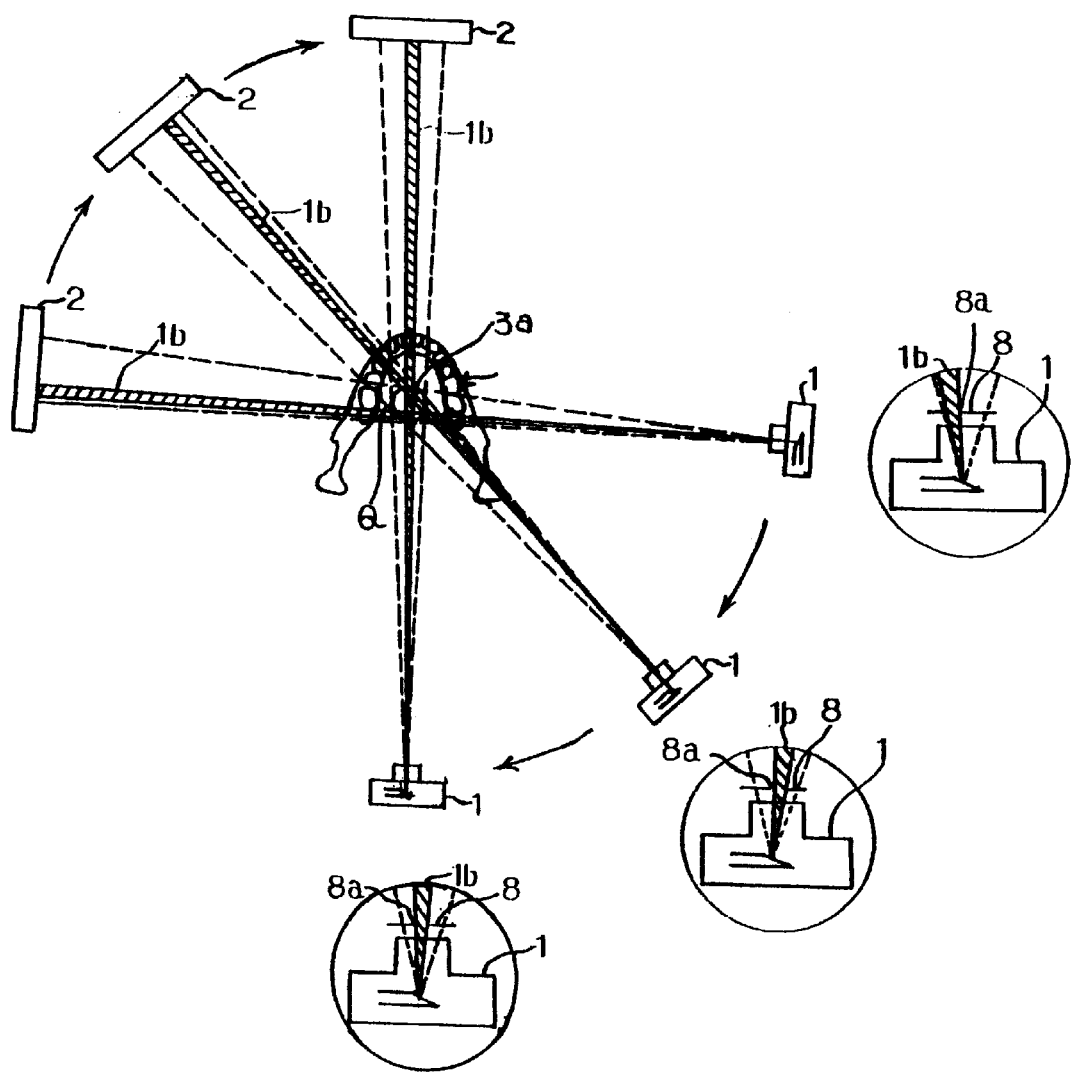
FIG. 6 shows an X-ray CT projection method for producing a panorama image using a radiation control slit according to the present invention.

FIG. 5 and FIG. 6 show an ortho X-ray CT method for producing a panorama image of the present invention.

In FIG. 5 the center 3a of the rotary arm 3 and the width of the conical X-ray beam are fixedly supported so as to form the virtual local region Q shown in the figure and the rotary arm 3 is rotated at a constant velocity. While the X-ray generator 1 radiates a conical X-ray beam 1a having a fixed width in a scanning direction according to rotation of the arm 3, an X-ray projection image of the dental arch S is sequentially produced on the two-dimensional X-ray image sensor 2 by the conical X-ray beam 1a. Thus produced X-ray projection image extracts only a partial X-ray projection image produced by the conical X-ray beam 1b approximately orthogonal to the dental arch S among the radiation bundle of the conical X-ray beam 1a. The extracted partial X-ray projection image is processed and the three-dimensional X-ray absorption coefficient distribution information is taken out as an image information, thereby the panorama image of the dental arch S is produced.

Accordingly, a basic X-ray CT is executed wherein the rotary arm 3 is rotated with its center 3a fixed, simultaneously conical X-ray beam 1a with a fixed width is locally radiated, and a panorama image can be also produced.

In FIG. 6, like FIG. 5, the rotary arm 3 is rotated at a constant velocity with its center 3a and the width of the conical X-ray beam 1a fixedly supported so as to form the virtual local region Q. The X-ray generator 1 radiates only the conical X-ray beam 1b orthogonal to the dental arch S through a slit window 8a by controlling synchronous transferring of a radiation control slit 8 in the direction orthogonal to the conical X-ray beam 1a depending on the change of rotational angle of the arm 3. Accordingly only the partial X-ray projection image projected on the two-dimensional X-ray image sensor 2 is extracted, the extracted image is processed, three-dimensional X-ray absorption coefficient distribution information of the dental arch S is taken out as a image information, and the panorama image of the dental arch S is produced.

Thus, in addition to the effect of FIG. 5, X-ray exposed dose of the object can be reduced as the rate that a conical X-ray beam is changed to a conical X-ray beam.

Figure 7A:
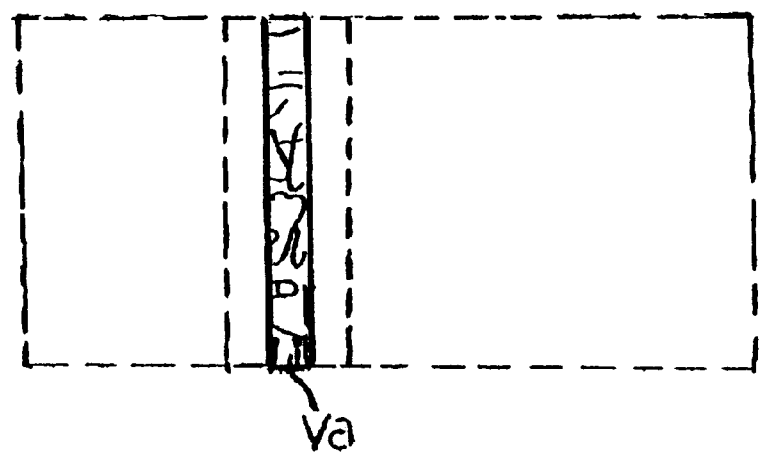
FIG. 7 is a partial X-ray image of a dental arch.
FIG. 7(b) explains a panorama image of a dental arch.
Figure 7B:
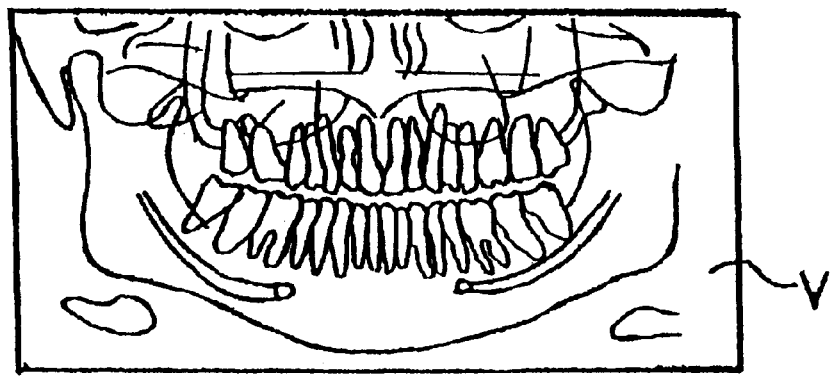

FIG. 7(a) shows an X-ray partial panorama image Va produced from a partial X-ray projection image further extracted from the X-ray projection image produced on the two-dimensional X-ray image sensor 2 or from the partial X-ray projection image directly projected on the two-dimensional X-ray image sensor 2 after backprojection processing and extracting the X-ray absorption coefficient distribution information according to the present invention. FIG. 7(b) shows an example of a panorama image V produced by aligning and combining the X-ray partial panorama image Va.

Next, the X-ray CT system of the present invention will be described hereinafter.

Figure 8:
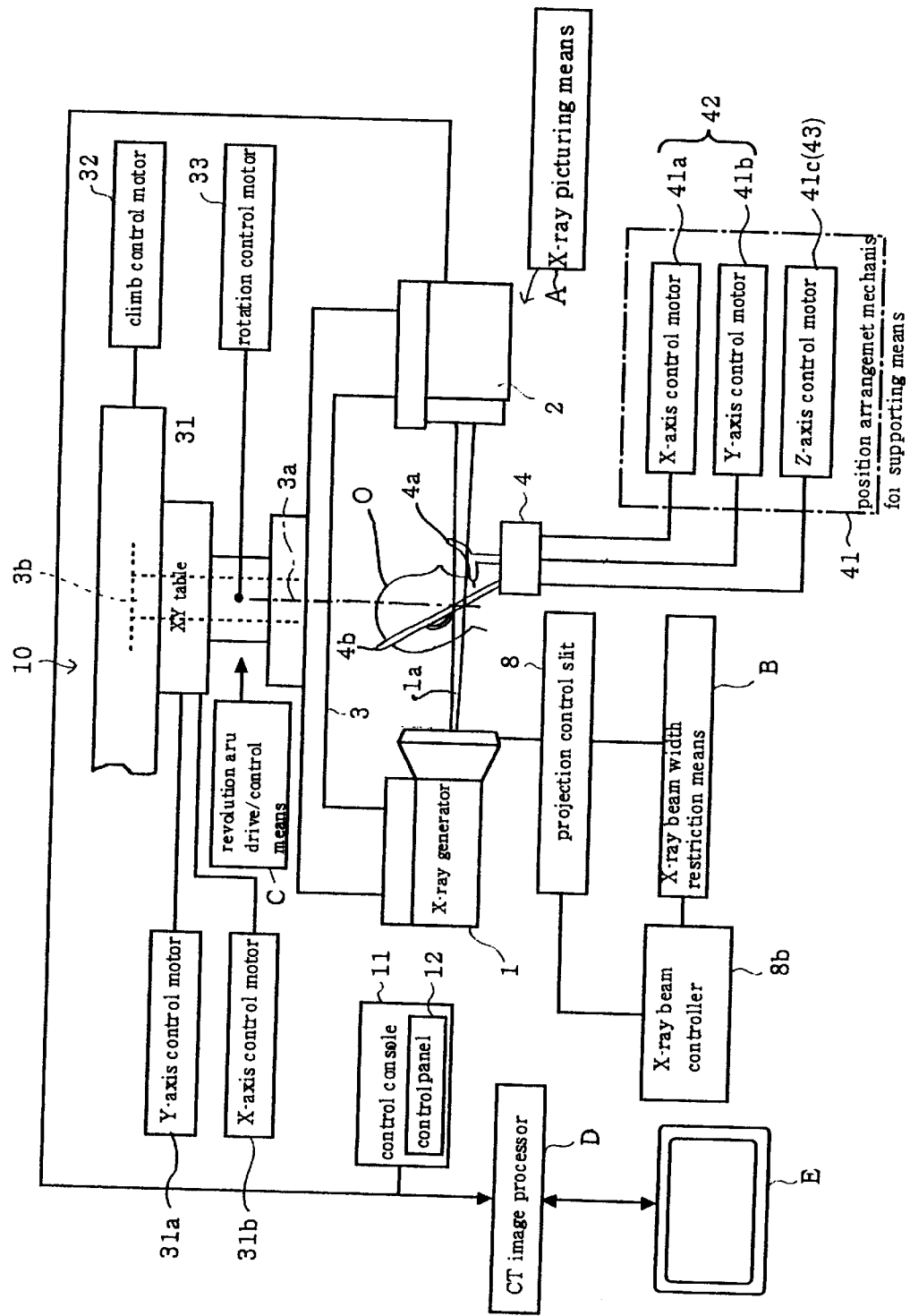
FIG. 8 shows basic construction of an X-ray CT system of the present invention.

FIG. 8 is a block diagram showing a rough construction of the X-ray CT system of the present invention.

The X-ray CT system 20 is comprised of projection means A, an X-ray beam width restriction means B, a drive and control means for a rotary arm C, an image processor D, a display E, an object holding means 4, a main frame 10, an operation console 11, a control panel 12 and so on.

The projection means A is provided with a rotary arm 3 and the arm 3 is located such that the X-ray generator 1 and the two-dimensional X-ray image sensor 2 are opposing and suspending.

The X-ray generator 1 is provided with the X-ray beam width restriction means B having the radiation control slit 8 and an X-ray beam controller 8b. The X-ray beam projected from an X-ray tube is adjusted by the X-ray beam width restriction means B and a conical X-ray beam 1a or a conical X-ray beam 1b with a desired beam width is designed to be radiated. It will be detailed hereinafter.

A well-known two-dimensional X-ray image sensor 2 is used wherein an optical fiber element for transmitting an optical image is provided on a MOS image sensor arranging a photodiode two dimensionally and further a scintillator layer for converting an X-ray to a visible ray is formed thereon. It will be also detailed hereinafter.

The rotary arm 3 is provided with an XY table 31, a climb control motor 32, and a rotation control motor 33. The center 3a of the arm 3 can be set in X, Y direction by controlling an X-axis control motor 31a and a Y-axis control motor 31b. The arm 3 is designed to go up and down by driving the climb control motor 32 and to be rotated around the object O by driving the rotation control motor 33 at a constant velocity in case of roentgenography. The climb control motor 32 comprises an adjusting means of up and down position of the arm 3.

The center 3a of the rotary arm 3, namely a rotary axis, is provided vertically, the arm 3 is rotated horizontally, and the conical X-ray beam 1a is horizontally and locally radiated. Therefore, the system can be constructed as a vertical type which requires a little occupied floor area.

The rotation control motor 33 is comprised as a rotation driving means of the rotary arm 3, uses a motor freely controllable its rotary speed and rotary position, and is positioned so as to be directly connected to the center 3a of the rotary arm 3 by the axis.

Therefore, the arm 3 can be rotated at a constant velocity and its position can be known along a time axis. It is preferable to take out an X-ray projection image by the two-dimensional X-ray image sensor 2 at an exact timing, there is no core deflection, thereby the X-ray CT method of the present invention can be effectively executed.

The center 3a of the rotary arm 3 is provided with a hollow 3b. All the associated parts provided for the center 3a should be hollow aperture respectively so as to provide the hollow 3b. For example, a servo motor with a hollow axis can be used as the rotation control motor 33 for this purpose.

The hollow 3b is formed for disposing a connecting line between the X-ray generator 1 and the two-dimensional X-ray image sensor 2 both suspending from the rotary arm 3 and the operation console 11 provided at the main frame 10 side.

When an electrical wiring is connected for a rotation part, its wiring method becomes a problem. However, when the electrical wire is disposed through the center 3a of the rotary arm 3, affect such as twisting caused by rotation can be minimized and further such an arrangement has anaesthetic preferable effect.

The driving and controlling means for a rotary arm C is constructed by combining the XY table 31, the climb control motor 32 and the rotation control motor 33 in this embodiment. However, the invention isn't limited to such a construction. As a most simple construction, the center 3a of the rotary arm 3 can be set at an optional position by operating a manual handle.

The XY table 31 for horizontally moving and setting the center 3a of the rotary arm 3 is provided for positioning the center 3a at the center Pa of the local region P in the object O by an X-ray CT. When the object holding means 4 with a holding means adjusting mechanism 41, will be described hereinafter, is provided, such an arrangement can be done at the object side. Therefore, such an XY table 31 isn't always required.

When only a panorama X-ray projection is executed, the center 3a of the rotary arm 3 is simply fixed around the center of the dental arch S, therefore, the XY table 31 isn't required. Further, the holding means adjusting mechanism 41 isn't required for the object holding means 4. Accordingly the system can be constructed simply.

The object O (here a human head is used as an example) places his lower jaw on a chin rest 4a of the object holding means 4, inserts the tips of ear rods 4b in both conchae, thereby the head is properly positioned. The object holding means 4 is provided with the holding means adjusting mechanism 41 having an X-axis control motor 41a, a Y-axis control motor 41b, and a Z-axis control motor 41c. The vertical position is adjusted according to the height of the object O and the longitudinal position is set so as to locate the object O at an appropriate position for projection.

The object holding means 4 is placed on the combined table (not shown) of an X-axis linear movable table, a Y-axis linear movable table, and a Z-axis linear movable table provided with the X-axis control motor 41a, a Y-axis control motor 41b, and a Z-axis control motor 41c respectively. These linear movable tables are comprised of a well known cross roller guide and a combination of a regular bearing and a guide respectively and can linearly move accurately. Although rack and pinion system, a ball screw system, and a normal screw axis system can be used to move these tables, accurately positioning system is desirable.

An object horizontal position adjustment means 42 is comprised of the X-axis control motor 41a and the Y-axis control motor 41b with such linear movable tables and driving systems and an object vertical position adjustment means 43 is comprised of the Z-axis control motor 41c.

Thus, the object horizontal position adjustment means 42 for freely setting the horizontal position of the object O and the object vertical position adjustment means 43 provided for freely setting the vertical position of the object O are provided. The height of the object holding means 4 can be adjusted at the height of the object O. Further, it is advantageous to adjust the center Pa of the local region P in the object O to the center 3a of the rotary arm 3.

As mentioned above, if the rotary arm 3 is provided with the XY table 31 for moving the center 3a thereof and the climb control motor 32, the object horizontal position adjustment means 42 isn't always required. However, sometimes it may be advantageous that the rough position of the object O is adjusted by the object horizontal position adjustment means 42 and the object position adjustment means 43 and then fine adjustments are done by the XY table 31 and the climb control motor 32 provided for the rotary arm 3, thereby both may be provided.

As an adjusting means for the object O, other than the above-mentioned, a chair on which the object O (here it is a patient having the head) and together the object holding means 4 may be moved so as to be positioned. In such a case, the position of the patient can be gently positioned while sitting on a chair.

The image processor D includes an arithmetic processor operating an image process analysis at high speed and the absorption coefficient distribution information in the object through which an X-ray passes is calculated by executing a predetermined arithmetic operation after pre-processing the X-ray projection image produced on the two-dimensional X-ray image sensor 2. Then an optional sectional image and a panorama image of the projected local region P are shown by the display E and they are stored in a necessary storage medium as a image information.

On the display E a three-dimensional perspective view of the local region P is shown in advance so as to be rotatable in X, Y and Z directions respectively and it is designed that the sectional image is displayed by specifying the section on the display where a doctor or an operator want to diagnose. Therefore, it is convenient for selecting a desired section and the internal condition of the front jaw, the back jaw, and tooth projected as the local region P of the object O can be judged accurately.

The main frame 10 is a structure supporting the whole system 20 and will be detailed hereinafter. The operation console 11 controls the whole system 20 and executes several controls and commands receiving an input from the control panel 12.

The control panel 12 is provided for inputting necessary data for the system 20 and operating procedures and will be detailed hereinafter.

Figure 9:
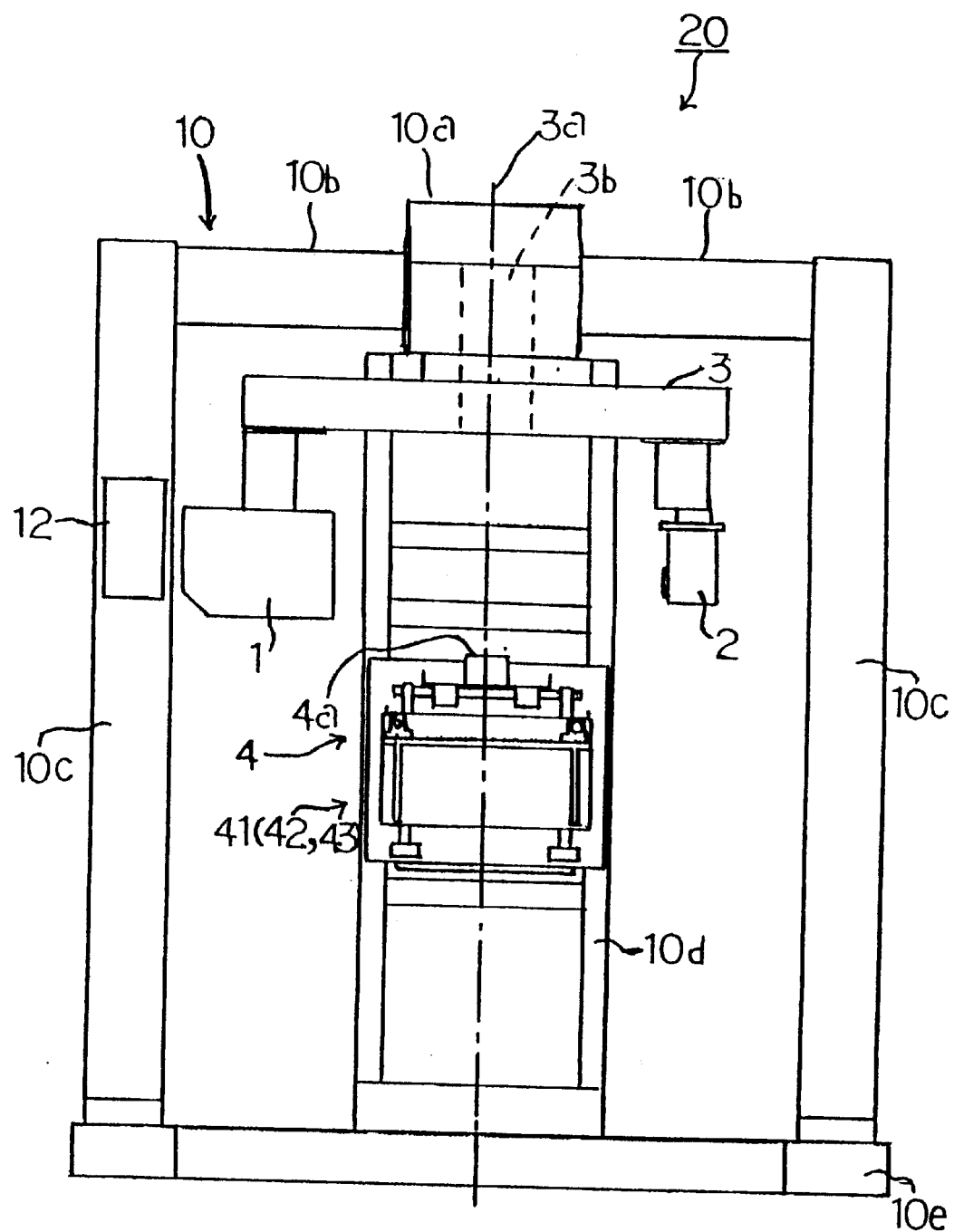
FIG. 9 is an external front view of an example of an X-ray CT system of the present invention.
Figure 10:
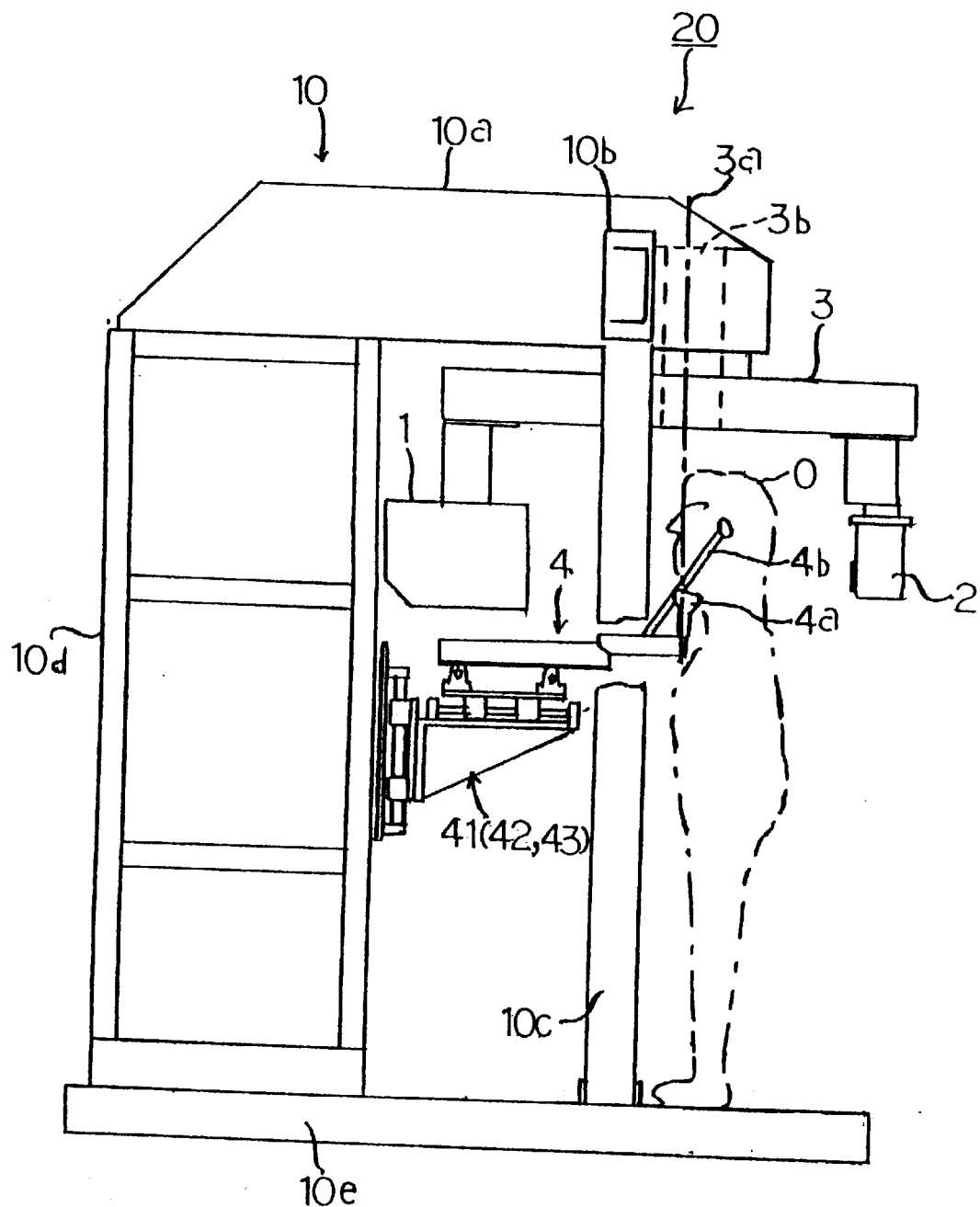
FIG. 10 is a external side view of an example of an X-ray CT system of the present invention.

FIG. 9 is an external front view of an example of an ortho X-ray CT of the present invention. FIG. 10 is its external side view. The members already explained are referenced as the same reference numbers and characters and their explanations are omitted hereinafter.

The X-ray CT system 20 is provided with the main frame 10 which is a highly rigid structure like a gate as a support for the whole system. The main frame is comprised of an arm 10a rotationally supporting the rotary arm 3 suspending the X-ray generator 1 and the two-dimensional X-ray image sensor 2 opposing each other, a pair of lateral beams 10b for fixing the both sides around the rotary arm supporting area of the arm 10a to prevent deflection caused by rotation of the arm 3, a pair of vertical beams 10c for supporting the lateral beams 10b, a column 10d for fixedly placing the arm 10a, and a base 10e on which the column 10d and the pair of vertical beams 10c are placed and is a base of the system 20.

These members comprising the main frame 10 are made of highly rigid steel and are strong for deformation by appropriately providing a diagonal brace and a reinforcing material for angles. Especially the arm 10a for rotationally supporting the rotary arm 3 is a highly rigid structure by itself, further, the pair of lateral beams 10b, the pair of vertical beams 10c are provided at the rotary support so as to prevent rotary deflection. Therefore, the center 3a of the rotary arm 3 doesn't move when rotating.

Thus, the main frame 10 is preferable for an ortho X-ray CT system especially requiring no deflection because it is a structure without causing deflection caused by the rotary arm 3.

The main frame 10 may not be provided with the lateral beam 10b and the vertical beam 10c if it is a rigid structure.

The control panel 12 is provided at the surface of anti-column 10d side of one of the vertical beams 10c of the main frame 10 and where the operator can easily operate while standing.

Figure 11:
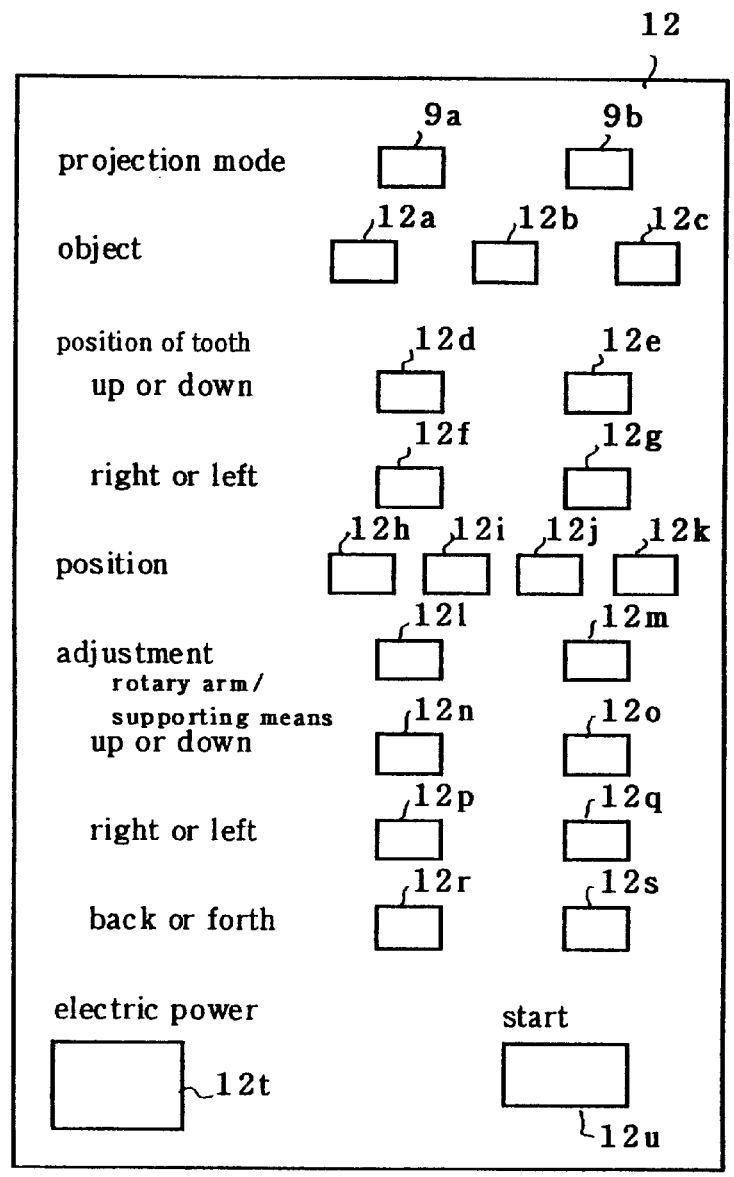
FIG. 11 is a front view showing a control panel of an X-ray CT system of the present invention.

FIG. 11 is a front view showing the control panel of the X-ray CT system of the present invention.

The control panel 12 is provided with a selection switch 9 for selecting the projection mode of the X-ray CT system. The switch 9 is comprised of a partial CT projection mode switch 9a and a panorama projection mode switch 9b for exclusively switching each other. When the partial CT projection mode switch 9a is operated, an optical sectional image of the local region is produced by a normal X-ray CT. When the panorama projection mode switch 9b is operated, a panorama image of the dental arch S is produced by the X-ray CT for producing a panorama image.

As mentioned above, according to the X-ray CT of the present invention, when a panorama image is produced, the center 3a of the rotary arm 3 may be fixed at a predetermined position as it is and its rotary angle and the width of a conical X-ray beam are changed and slit control is executed. Therefore, the X-ray CT system which can produce both panorama image and a sectional image can be simply constructed.

In stead of providing such a selection switch 9, the sensor used for the two-dimensional X-ray image sensor 2 may be a cassette type and a different cassette is prepared for a normal X-ray CT and for a panorama image producing X-ray CT. And the partial CT projection mode and the panorama projection mode may be changed by exchanging the cassettes.

Selection switches for an object 12a, 12b, 12c are provided under the selection switch 9. These switches 12a, 12b, 12c are used by combining with selection switches for positioning a tooth 12d–12g provided thereunder and used for positioning the object holding means 4 at an appropriate position (see FIG. 8) according to the projection mode. The switch 12a is operated when the object O is a small child, the switch 12b is operated for an average child, and the switch 12c is operated for an adult.

The switches 12d, 12e are used for selecting whether the local region P to be projected is an upper jaw or a lower jaw. When the switch 12d is operated, an upper jaw is selected and the switch 12e is operated, a lower jaw is selected. The switches 12f and 12g are for selecting right or left of the local region P. When the switch 12f is operated, a left jaw is selected and when the switch 12g is operated, a right jaw is selected.

The switches 12h–12k thereunder are for selecting further detailed position of the local region P to be projected. When the switch 12h is operated, the first tooth and the second tooth on the basis of the axis of symmetry Lo of the dental arch S are selected. The third and the fourth teeth are selected when the switch 12i is selected, the fifth and the sixth teeth are selected when the switch 12j is operated, and the seventh and the eighth teeth are selected when the switch 12k is operated.

The adjustment switches 12l–12s are for adjusting the position of the rotary arm 3 or the position of the object holding means 4.

The rotary arm 3 is selected as an adjustment object when the switch 12l is operated, the supporting means for the object 4 is selected when the switch 12m is operated.

When the switch 12l is operated and also switches 12n and 12o are operated, the climb control motor 32 is driven and the rotary arm 3 goes up and down. When the switches 12p and 12q are operated together with the switch 12i, the X-axis control motor 31a is driven and the rotary arm 3 moves laterally. When the switches 12r, 12s are operated together with the switch 12l, the Y-axis control motor 31b is driven and the rotary arm 3 moves back and forth.

When the switch 12m is operated and switches 12n and 12o are also operated, the Z-axis control motor 41c of the holding means adjusting mechanism 41 is driven and the object holding means 4 goes up and down. When the switches 12p and 12q are operated together with the switch 12m, the X-axis control motor 41a is driven and the object holding means 4 moves laterally. When the switches 12r and 12s are operated together with the switch 12m, the Y-axis control motor 41b is driven and the object holding means 4 moves back and forth.

An electric power switch 12t provided at the bottom is for turning on and off the electric power of the whole system 20. A start switch 12u is for starting projection.

Thus, the X-ray CT system 20 can be set and operated by the control panel 12.

Figure 12:
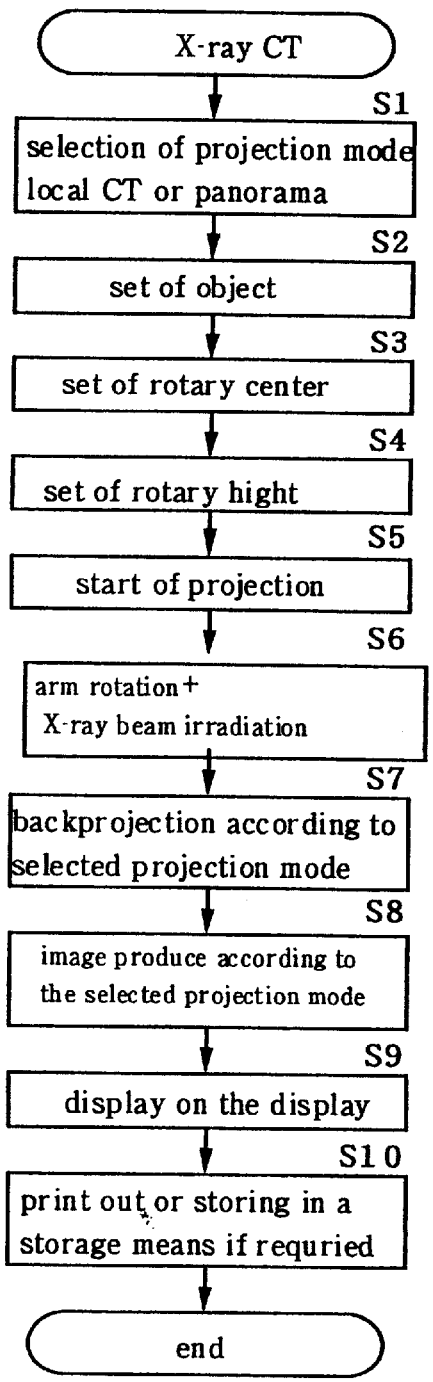
FIG. 12 is a flow chart showing projection procedures of an X-ray CT system of the present invention.

FIG. 12 is a flow chart showing projection procedures of the ortho X-ray CT system of the present invention. Referring to the flow chart, projection procedures will be explained.

The local CT projection mode or the panorama projection mode is selected by the selection switch 9 of the control panel 12 (S1). The object O is placed on the chin rest 4a of the object holding means 4 (S2). The center 3a of the rotary arm 3 is set at the center Pa of the local region P of the object O at the local CT projection mode, and the center 3a is set at the center Qa of the virtual local region Q of the object O at a panorama projection mode (S3).

Then the height of the rotary arm 3 is adjusted so that the vertical height of the conical X-ray beam 1a locally radiated from the X-ray generator 1 is set in the local region P or the virtual local region Q (S4). Projection is started and the conical X-ray beam 1a is locally radiated according to the projection mode while the rotary arm 3 is rotated within a fixed angle area corresponding to the projection mode (S5, S6, S7)

As explained in the X-ray CT method, an image processing including backprojection is executed according to the projection mode (S7), a sectional image or a panorama image is produced (S8), the image is displayed on the display E (S9), the image is printed out or stored in the storing means if necessary (S10), and the procedure finishes.

Next an X-ray beam width restriction means will be described.

According to the X-ray CT method of the present invention, when the local region to be projected is specified, it is required that the beam width of the conical X-ray beam 1a radiated from the X-ray generator 1 is adjusted and further the center 3a of the rotary arm 3 is set at a position corresponding to the position of the local region.

The X-ray beam width restriction means B is provided for the above-mentioned purpose and the vertical and lateral dimensions of the X-ray bundle radiated from an X-ray source of the X-ray generator 1 at a fixed radiation angle are restricted. This adjustment can be made manually or automatically by operating setting switches.

As such an X-ray beam width restriction means B, there is a system or means wherein a slit control plate (not shown) with a plural window slits is set before the X-ray generator 1 and the slit control plate is slid or a plurality of a first slit with different window openings are prepared and the conical X-ray beam completely including only the local region to be projected is defined from them. If the window opening is formed with a plural members independently movable each other, an optional window opening can be formed by adjusting these members.

Figure 13:
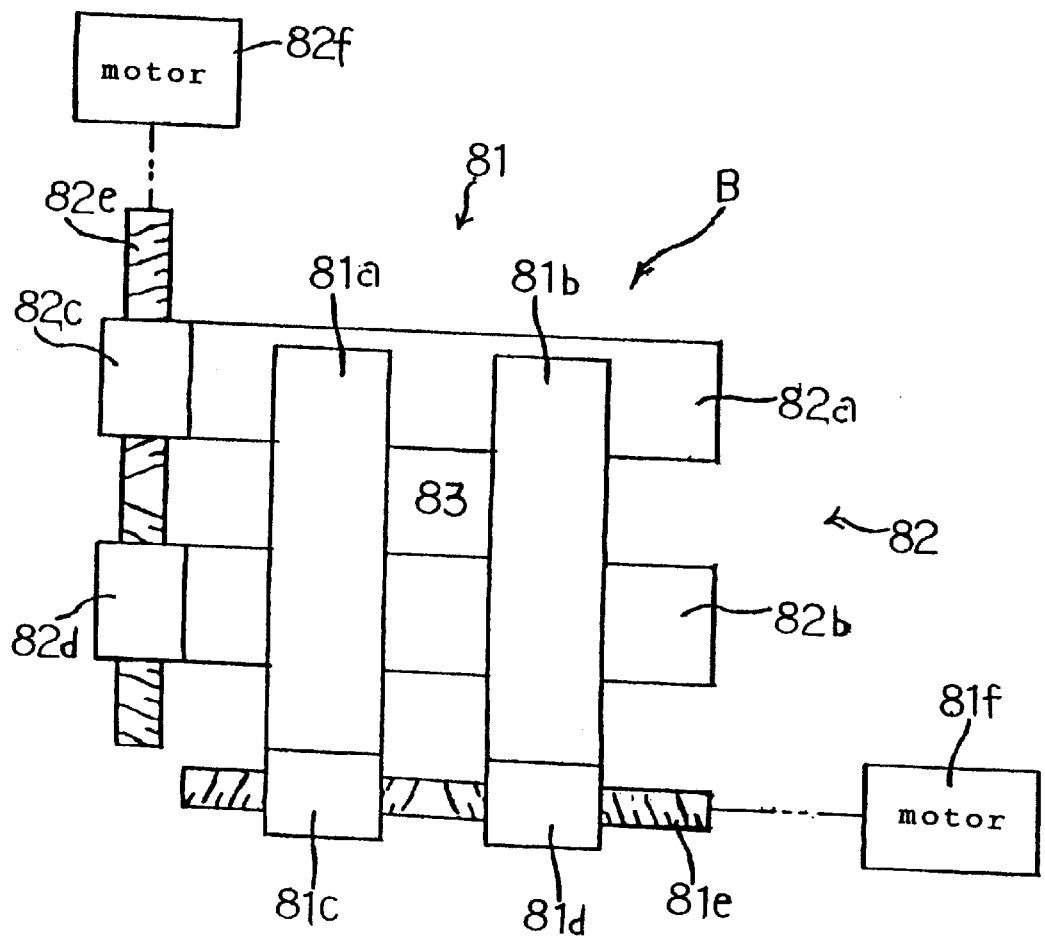
FIG. 13 is a front view of a substantial part of one embodiment of an X-ray beam width restriction means.

FIG. 13 is a front view of a substantial part of one embodiment of the X-ray beam width restriction means. FIG. 14 is a front view of a substantial part showing a restriction condition of the X-ray beam width restriction means.

The X-ray beam width restriction means B is comprised of a lateral direction restriction means 81, vertical direction restriction means 82, and a slit hole 83.

The lateral direction restriction means 81 is comprised of a pair of right and left slit plates 81a, 81b, female screws 81c, 81d provided for each slit plate, a screw axis 81e for screwing these female screws 81c, 81d, and a lateral motor 81f for rotatably driving the screw axis 81e. The female screws 81c, 81d are comprised of a pair of a right screw and a left screw respectively and correspondingly a male screw comprised of a right screw and a left screw is formed at the screw axis 81e for parting from the center of the longitudinal direction.

Therefore, when the lateral motor 81f is driven and rotated, the right and left slit plates 81a, 81b are approached or departed each other at the same distance and the lateral width of the slit hole 83 is restricted centrosymmetrically.

The vertical direction restriction means 82 is comprised of a pair of a upper and lower slit plates 82a, 82b, female screws 82c, 82d provided for each slit plate, a screw axis 82e for screwing the female screws 82c, 82d, and a vertical motor 82f for driving and rotating the screw axis 82e and is positioned so as to be orthogonal with the lateral direction restriction means 81. The female screws 82c, 82d are comprised of a pair of a right screw and a left screw respectively and correspondingly a male screw comprised of a right screw and a left screw is formed at the screw axis 82e for parting from the center of the longitudinal direction.

Therefore, when the vertical motor 82f is driven and rotated, the upper and lower slit plates 82a, 82b are approached or departed each other at the same distance and the vertical width of the slit hole 83 is restricted centrosymmetrically.

Thus, the width of the slit hole 83, namely the vertical and lateral widths of the conical X-ray beam, can be restricted by the X-ray beam width restriction means B.

Figure 14A:
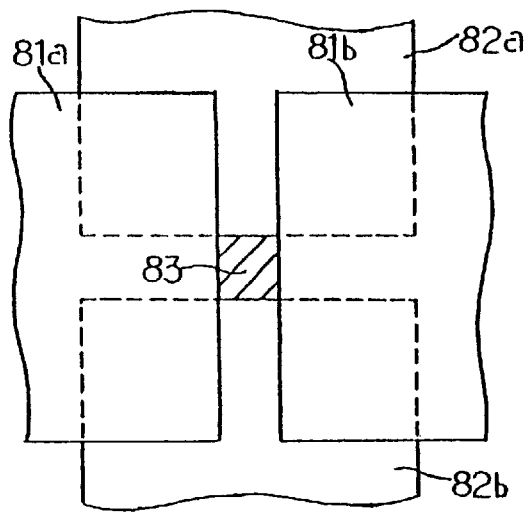
FIG. 14 is a front view of a substantial part showing restriction condition of an X-ray beam width restriction means.
Figure 14B:
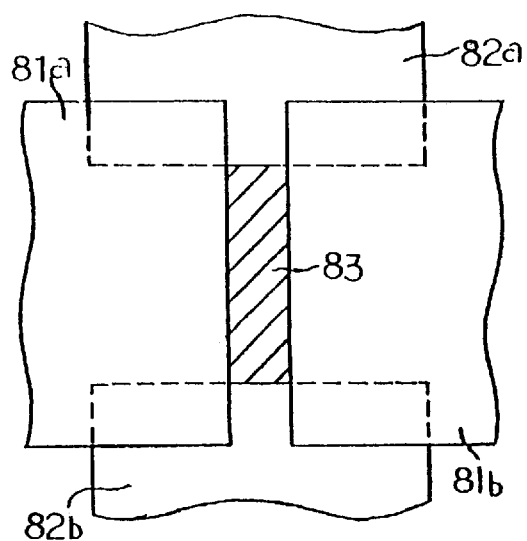

In FIG. 14(a) the vertical width and the lateral width of the slit hole 83 are made small and in FIG. 14(b) the slit hole 83 is made rectangular.

Figure 15:
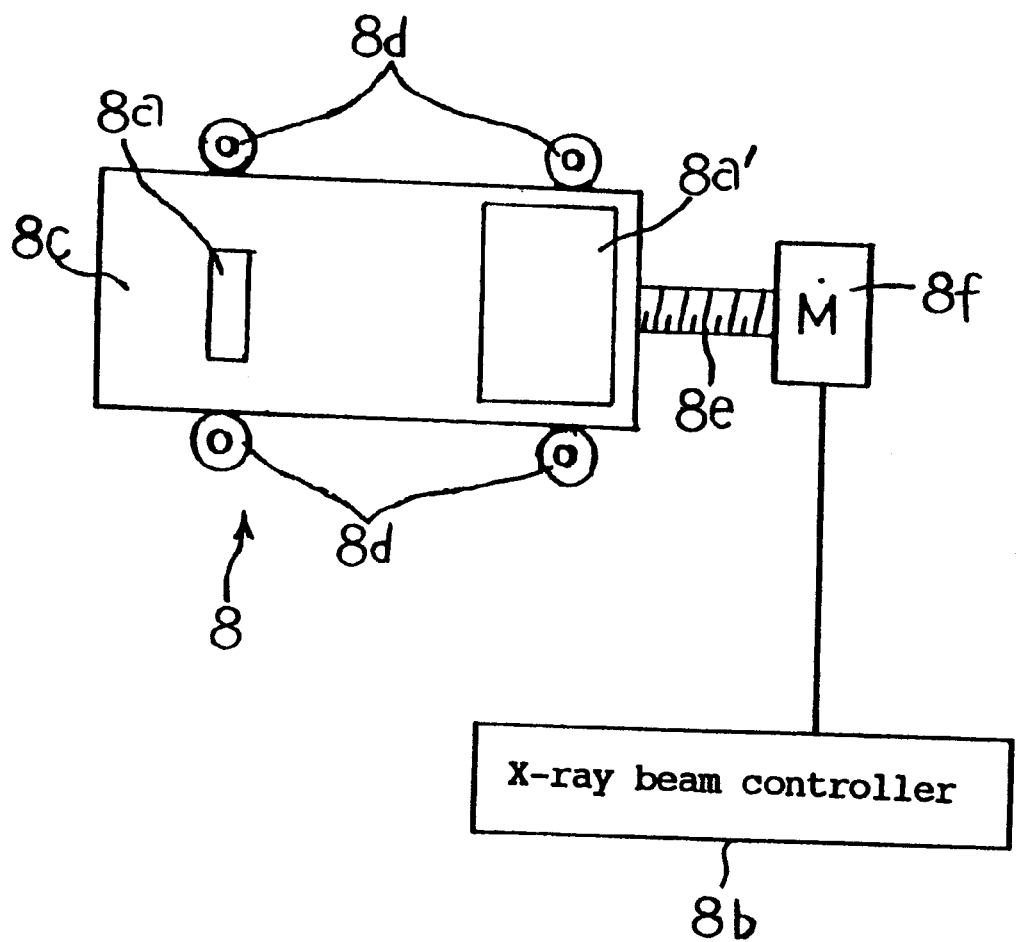
FIG. 15 is a partial front view showing one embodiment of a radiation control slit according to the present invention.

FIG. 15 is a substantial front view showing one embodiment of a radiation control slit according to the present invention.

The radiation control slit 8 is controlled by the X-ray beam controller 8b. The slit 8 is used by overlapping on the X-ray beam width restriction means B so that only the conical X-ray beam 1b is radiated from the conical X-ray beam 1a with its vertical and lateral width defined by the X-ray beam width restriction means B.

The radiation control slit 8 is comprised of a slit plate 8c having the slit window 8a and an open window 8a', four guide rollers 8d for reciprocating the slit plate 8c linearly, a screw axis 8e for screwing a female screw (not shown) provided for the slit plate 8c, and a control motor 8f for driving and rotating the screw axis 8e. Therefore, the position of the slit window 8a and the open window 8a can be freely controlled by controlling the control motor 8f by means of the X-ray beam controller 8b.

In normal X-ray CT, the slit plate 8c is moved so that the open window 8a' is overlapped on the slit hole 83 of the X-ray beam width restriction means B and the conical X-ray beam 1a produced by the X-ray beam width restriction means B is locally radiated.

In the X-ray CT for producing a panorama image, the slit window 8a is moved so as to overlap on the slit hole 83 of the X-ray beam width restriction means B and is controlled synchronizing with the rotation of the rotary arm 3 by the X-ray beam controller 8b so that only conical X-ray beam 1b among the conical X-ray beam 1a is radiated.

Thus, as explained in FIG. 6, only the conical X-ray beam 1b can be radiated.

Figure 16:
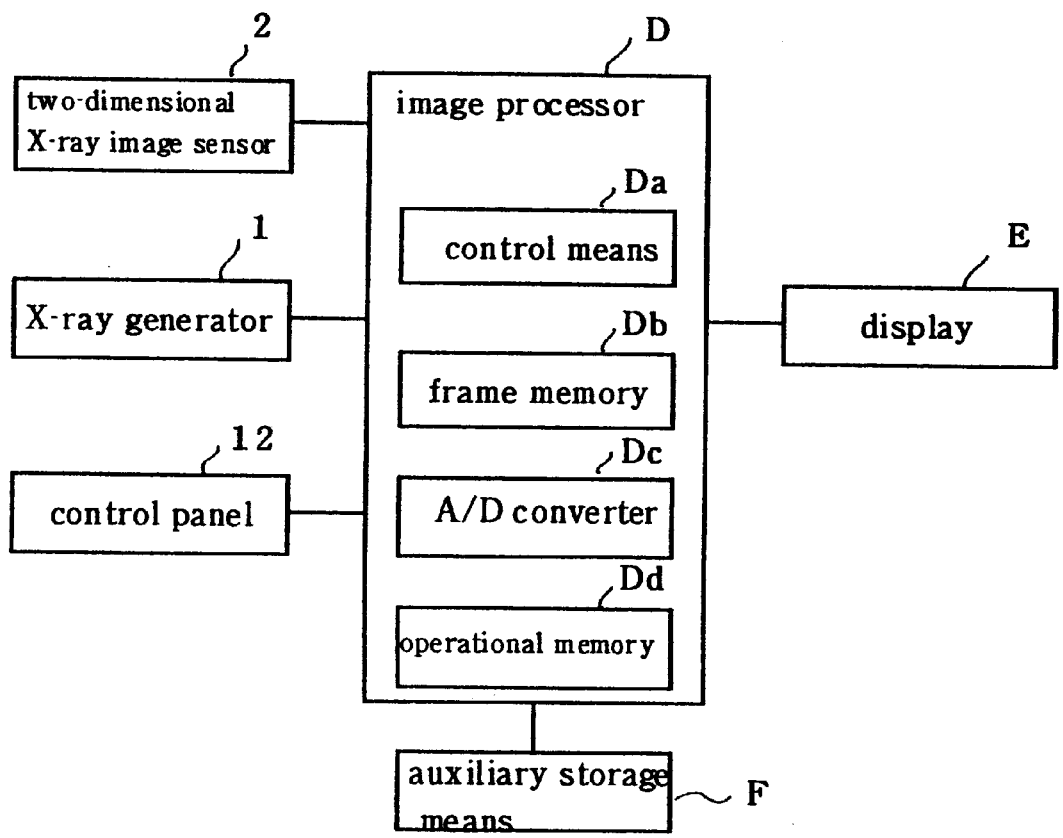
FIG. 16 is a block diagram showing the image processing system of an X-ray CT system according to the present invention.

FIG. 16 is a block diagram showing image processing of the ortho X-ray CT system of the present invention.

The process is executed by an image processor D as a main construction, the X-ray generator 1, the two-dimensional X-ray image sensor 2, the control panel 12, the display E, and an auxiliary storage means F. The image processor D is provided with a control means Da, a frame memory Db, and an A/D (analog to digital) converter Dc.

Such an image processor D may be comprised of a micro processor for image processing.

The image data received from the two-dimensional X-ray image sensor 2 is converted to a digital signal by the A/D converter Dc and the converted data is stored in the frame memory Db. A plural image data stored in the frame memory Db are stored in an arithmetic memory Dd, and a predetermined processing is executed for the stored image data corresponding to the selected projection mode. Then a sectional image or a panorama image is produced, displayed on the display E, and stored in the auxiliary storing means F if required.

A hard disc, a magnetic optical disc, and so on can be used as the auxiliary storing means F.

A MOS image sensor can be preferably used as the two-dimensional X-ray image sensor 2 and will be detailed hereinafter.

Figure 17C:
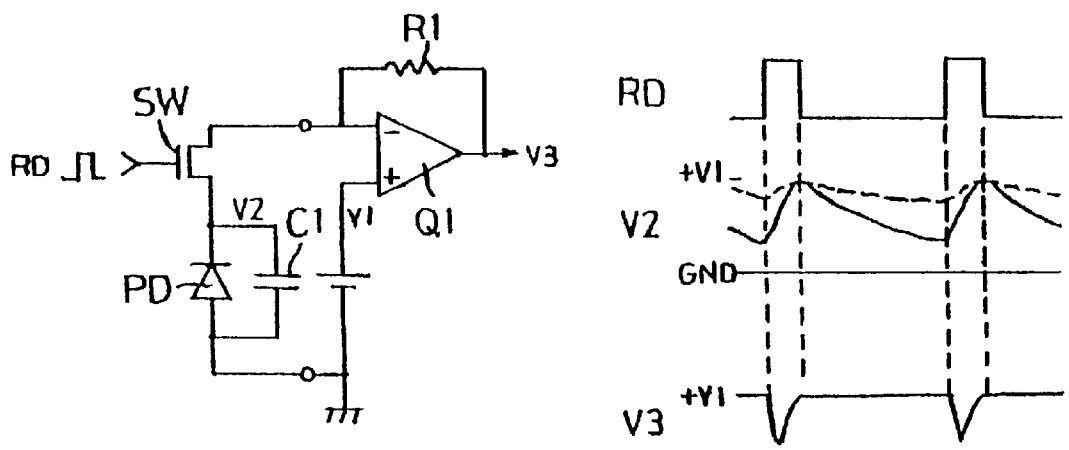
FIG. 17(c) is a sectional view showing the construction of a two-dimensional X-ray image sensor using MOS.
Figure 17C:
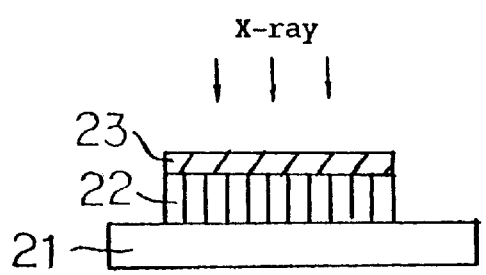

Referring to FIG. 17, the operational principle of the MOS image sensor and the construction of the two-dimensional X-ray image sensor using the MOS image sensor will be described.

In FIG. 17(a) a photodiode PD constructing a photo acceptance pixel converts the inserted light into an electrical signal. The photodiode PD is seriously connected by a switch SW comprised of MOSFET (metal-oxide semiconductor field-effect transistor) and is further connected to a reverse terminal of an operational amplifier Q1. The operational amplifier Q1 is connected to a feedback resistance R1, thereby comprising a current and voltage converter circuit from which an inputted current is outputted as a voltage signal. A voltage V1 is applied against the grand (GND) for an non-reverse terminal of the operational amplifier Q1.

In FIG. 17(b) when a positive reading pulse RD comes to a gate of the switch SW, the switch SW is opened, the photodiode PD becomes anti-bias, and a fixed amount of electricity is charged at a junction capacity C1. Then the switch SW is closed and the charged electricity is discharged by the electricity of the projected light when a light is projected during charge time, and a cathode electric potential of the photodiode PD approaches a grand electric potential. The discharged electric charge amount increases in proportion to the inserted light amount.

When the reading pulse RD comes to the gate of the switch SW and the switch SW is opened, the electric charge corresponding to the discharged electricity during charge time is supplied via the feedback resistance R1 and simultaneously the photodiode PD becomes anti-bias again to be initialized. In this time an electric potential difference is caused by the charged current at both ends of the feedback resistance R1 and outputted as a voltage signal from the operational amplifier Q1. The charged current corresponds to the discharged current by the inserted light so that the projected light amount is detected by the output voltage.

FIG. 17(c) is a sectional view showing a construction of the two-dimensional X-ray image sensor 2 using the MOS image sensor. An optical fiber element (FOP) 22 for transmitting an optical image is provided on the MOS image sensor 21 two-dimensionally arranging the photodiode PD to be a photo acceptance pixel, and further the scintillator layer 23 for converting an X-ray into a visible ray is provided thereon. The X-ray image passed through the object is converted to a visible light image, further transmitted by the optical fiber element 22, and photoelectrically converted by the MOS image sensor 21.

Figure 18:
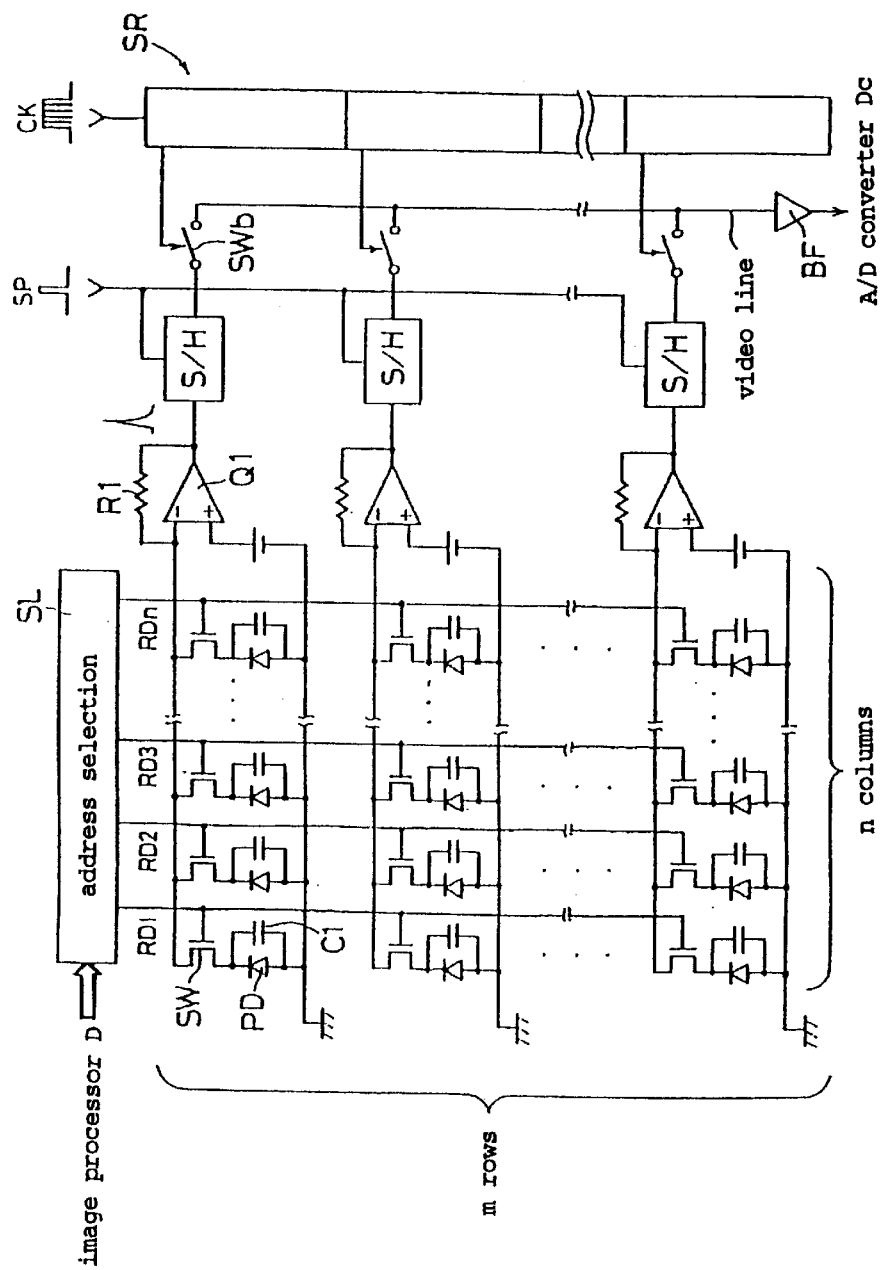
FIG. 18 shows a drive circuit for a MOS image sensor used for a two-dimensional X-ray image sensor according to the present invention.

FIG. 18 is a driving circuit for the MOS image sensor 21. The photodiode PD to be a photo acceptance pixel is arranged in a matrix of m-rows by n-columns, the junction capacity C1 is connected in parallel to each photodiode PD, and the reading switch SW is seriously connected. The gate of the switch SW is connected by an address selection circuit SL and the photodiode PD to be read out is selected based on the signal from the image processor D.

The output of the switch SW is commonly connected per a column and inputted to the operational amplifier Q1 comprising the current and voltage convert circuit. The output of the operational amplifier Q1 is sampled by a sample hold circuit (S/H). Each sample hold circuit is connected to a switch SWb operated by a shift register SR at m-step.

As each switch SWb is opened and closed in order, the sampled signal is outputted to the A/D converter DC of the image processor D as a time series signal. In such a case, a lag network may be provided between each arithmetic circuit Q1 and each sample hold circuit. The lag network integrates the current (or voltage) and the sample hold circuit samples the integrated amount.

If the lag network is provided, the output includes an integration time and the sensitivity of the detected signal can be increased.

Figure 19:
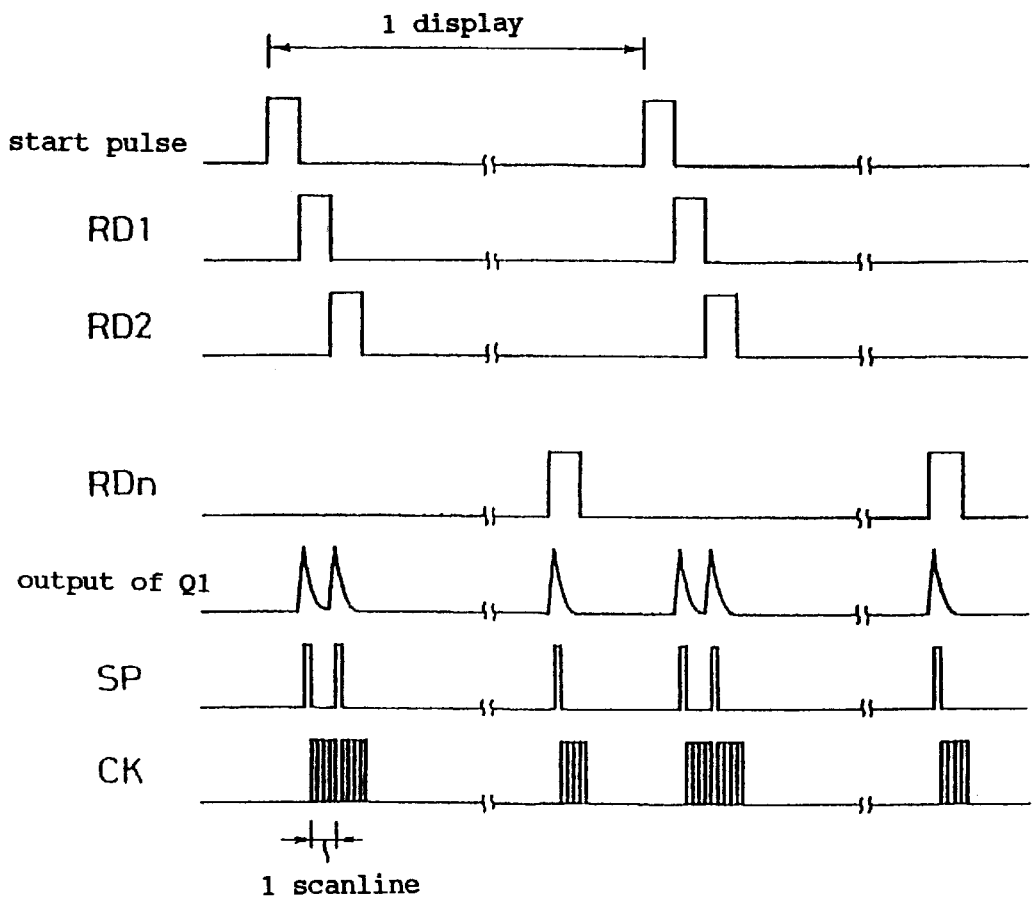
FIG. 19 is a timing chart showing the operation of a drive circuit of a MOS image sensor used for a two-dimensional X-ray image sensor according to the present invention.

FIG. 19 is a timing chart showing the operation of the driving circuit of FIG. 18.

Here an example using a shift register as the address selection circuit SL will be explained.

The address selection circuit SL is activated by a start pulse from the image processor D and sequentially output a reading pulse RD1 of the first column, a reading pulse RD2 of the second column, . . . , a reading pulse Rdn of the n-th column in synchronized with a reading clock from the image processor D.

For example, when the reading pulse RD1 of the first column is inputted into each gate of the switch SW of the first column, the electric charge corresponding to the projected light amount into each photodiode PD of the first column is read out and a voltage signal is outputted from the operational amplifier Q1. Then a sampling pulse SP is inputted into each sample hold circuit so as to sample a peak point of the output of the operational amplifier Q.

The sampled signal is transferred by a shift rock CK comprised of m-pieces of pulse before a next sampling pulse SP is inputted from the shift register SR and outputted outside as an image signal of one scanning line. As for other columns, a signal of m-rows is paratactic read out by one reading pulse and a time series signal of one scan-line is constructed by the shift register SR.

Figure 20:
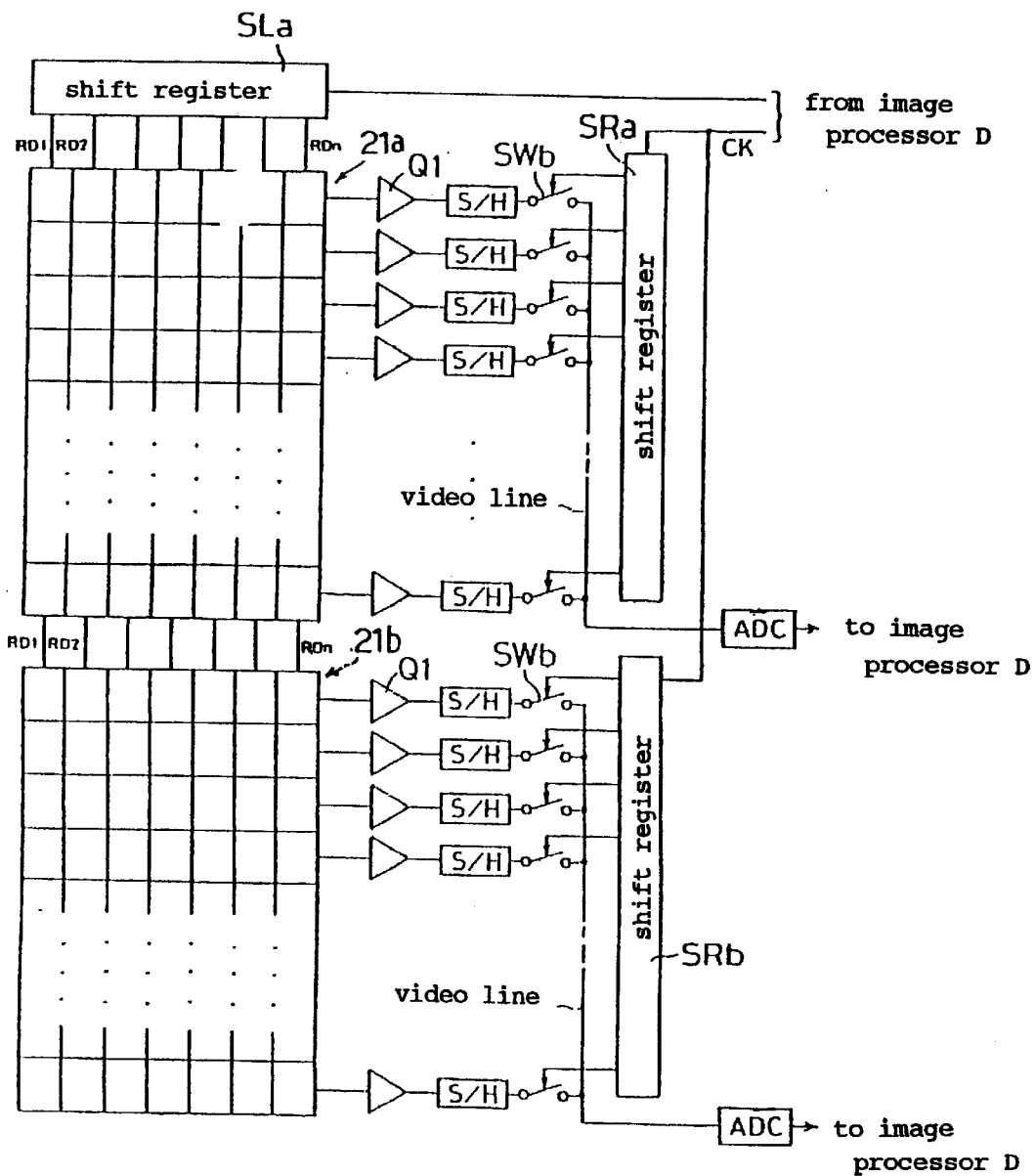
FIG. 20 shows a circuit diagram of an example wherein a MOS image sensor used for a two-dimensional X-ray image sensor of the present invention is connected in two-stage.

FIG. 20 is an example of a circuit wherein the MOS image sensor is connected in multi stage.

Two MOS image sensors 21a, 21b having a photo acceptance pixel of m-rows and n-columns are continuously arranged in a row direction and connected so that each reading pulse RD1–RDn from the shift register SLa comprising the address selection circuit SL is driven at the same column. A signal is read out from 2m-pieces of photodiodes by a reading pulse and inputted into 2m-pieces of operational amplifiers Q1 and sample hold circuits corresponding to each column.

Two shift registers SRa, SRb are disposed corresponding to the two MOS image sensor 21a, 21b and transfers the output from each sample hold circuit to the image processor D as a time serious signal by operating 2m-pieces of switch SWb in order. The signal supplied to the image processor D is converted to a digital signal by the A/D converter Dc and then stored in the frame memory Db.

In FIG. 20 two MOS image sensor 21a and 21b are used, however more than 3 stages of MOS image sensor may be connected.

The two-dimensional X-ray image sensors 2 used for the X-ray CT method for producing a panorama image of the dental arch S has a detecting surface, for example, about 30 cm long and about 10–30 cm wide. It preferably detects more than 30 pieces of X-ray projection image data or local X-ray projection image data per second.

As only a local X-ray projection image of the local region is preferably obtained when an X-ray CT method is used, the two-dimensional X-ray image sensor 2 can be minimized. Further, as the obtained X-ray projection image data is reduced, its processing speed becomes fast and the number of the X-ray projection image data detected in a fixed time is increased. Therefore, the whole system can be downsized and simultaneously projection speed can be fast.

Figure 21:
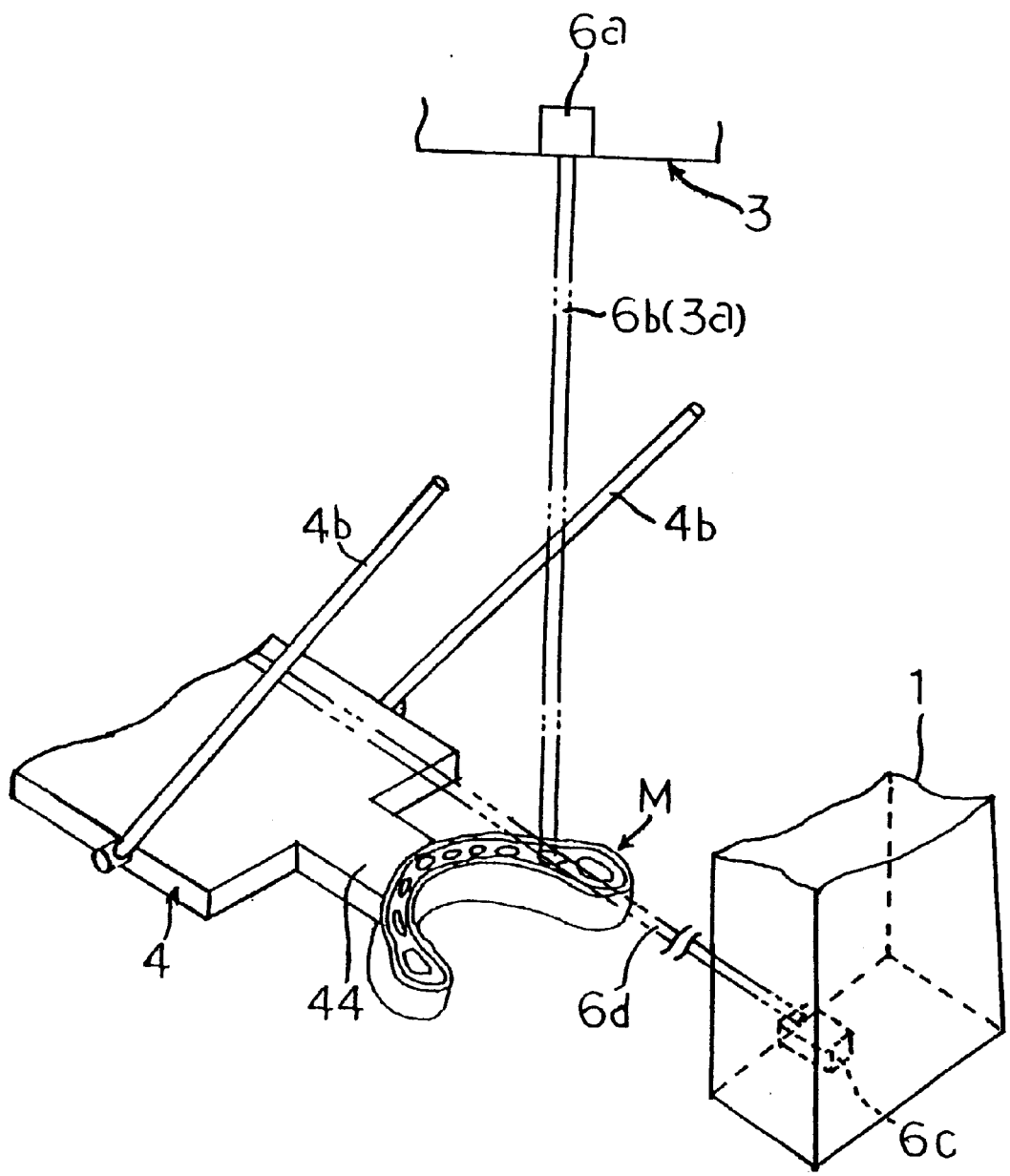
FIG. 21 is an explanatory view of a positioning method of the object for an X-ray CT using a dental articulation model and an optical beam radiation means according to the present invention.

FIG. 21 is an explanatory view of the positioning method of the object for the X-ray CT using a dental articulation model and a light beam irradiating means according to the present invention.

In the figure, the reference numeral 6a indicates a light beam irradiating means for a rotary center showing the center 3a of the rotary arm 3 as a beam 6b and 6c indicates a light beam irradiating means for an X-ray showing the irradiating axial core of a conical X-ray beam as a light beam 6d. Each of them is shown overlapping the center 3a or the irradiating axial core of the conical X-ray beam. The light beam irradiating means for a rotary center 6a and the light beam irradiating means for an X-ray 6b comprise an optical beam radiation means 6.

A fixing plate for the dental articulation model 44 is provided for the object holding means 4 instead of the chin rest 4a and the dental articulation model M is set at the tip of the support means 4.

The dental articulation model M is placed at the fixing plate for the dental articulation model 44 as shown in the figure, then the model M is positioned at an appropriate height by the Z-axis control motor 41c of the holding means adjusting mechanism 41 provided for the object holding means 4 supporting the model M so that the patient can fit the model M. Then the teeth of the dental articulation model M to be projected are positioned where the light beam 6b showing the center 3a of the optical beam radiation means 6 intersects the light beam 6d showing the irradiation axial core of the conical X-ray beam by adjusting the horizontal position by means of both or one of the object horizontal position adjustment means 42 of the holding means adjusting mechanism 41 and the XY table 31 at rotary arm side, thereby the position of the local region P is determined.

Thereafter, when the patient is going to bite the dental articulation model M, positioning of the local region P can be made accurately.

When the dental articulation model M isn't used, the chin rest 4a is provided for the object holding means 4 as shown in FIG. 10. In such a case positioning of the patient or the object O can be easily determined by means of the optical beam radiation means 6.

Figure 22:
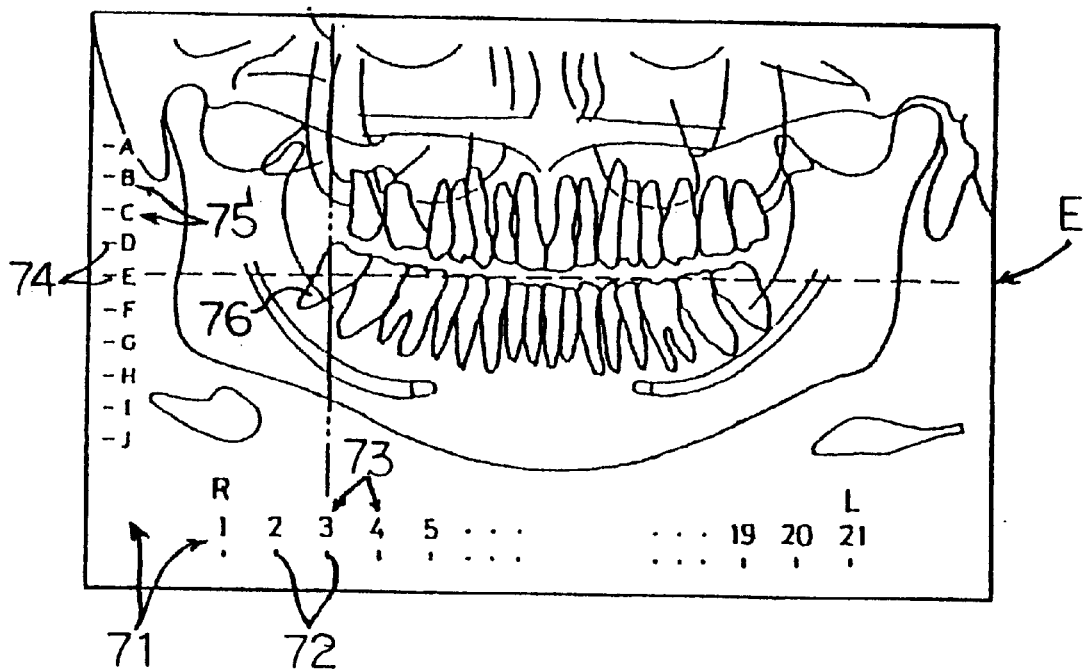
FIG. 22 is an explanatory view of the object positioning method for an X-ray CT system according to the present invention.

FIG. 22 is an explanatory view of another embodiment of the positioning method of the object for the X-ray CT system according to the present invention.

The figure shows a panorama image of the dental arch produced by the X-ray CT system of the present invention.

This panorama image is displayed on the display E of the X-ray CT system and a positional information 71 added by the image processor D is also shown.

The positional information 71 is comprised of a lateral gage 72 provided at practically regular intervals in direction of the circumference of the dental arch of the panorama image, a numerals 73 showing its position, a longitudinal gauge 74 vertical to the dental arch, and numerals 75 showing its position.

When the X-ray CT of a specific tooth comprising the dental arch is executed, a panorama image of the dental arch is projected as shown in the figure at first, then the local region P is preferably specified on the image. For example, when the X-ray CT of the tooth 76, a molar at left in a low arch as shown in the figure, is desired to be projected, "3" of the numerals 73 of the lateral gauge 72 and "E" of the numerals 75 of the longitudinal gauge 74 by means of an input means (not shown) provided for the display E are inputted.

Then positioning of the rotary arm 3 and the object O is carried out by means of the XY table 31, the climb control motor 32 of the rotary arm 3, and the object holding means adjustment mechanism 41 of the object holding means 4.

According to the X-ray CT method, an X-ray absorption coefficient at an optional point of the local region can be obtained. When such a coefficient is processed to be produced as a panorama image or a sectional image, the image proportional to the actual object can be obtained. Therefore, an optional position in the dental arch or teeth can be quantitatively represented as a position information by marking the image with degrees. It means the position of specific tooth or an implanted tooth can be quantitatively comprehended and it is a great help in a dental care.

Figure 23:
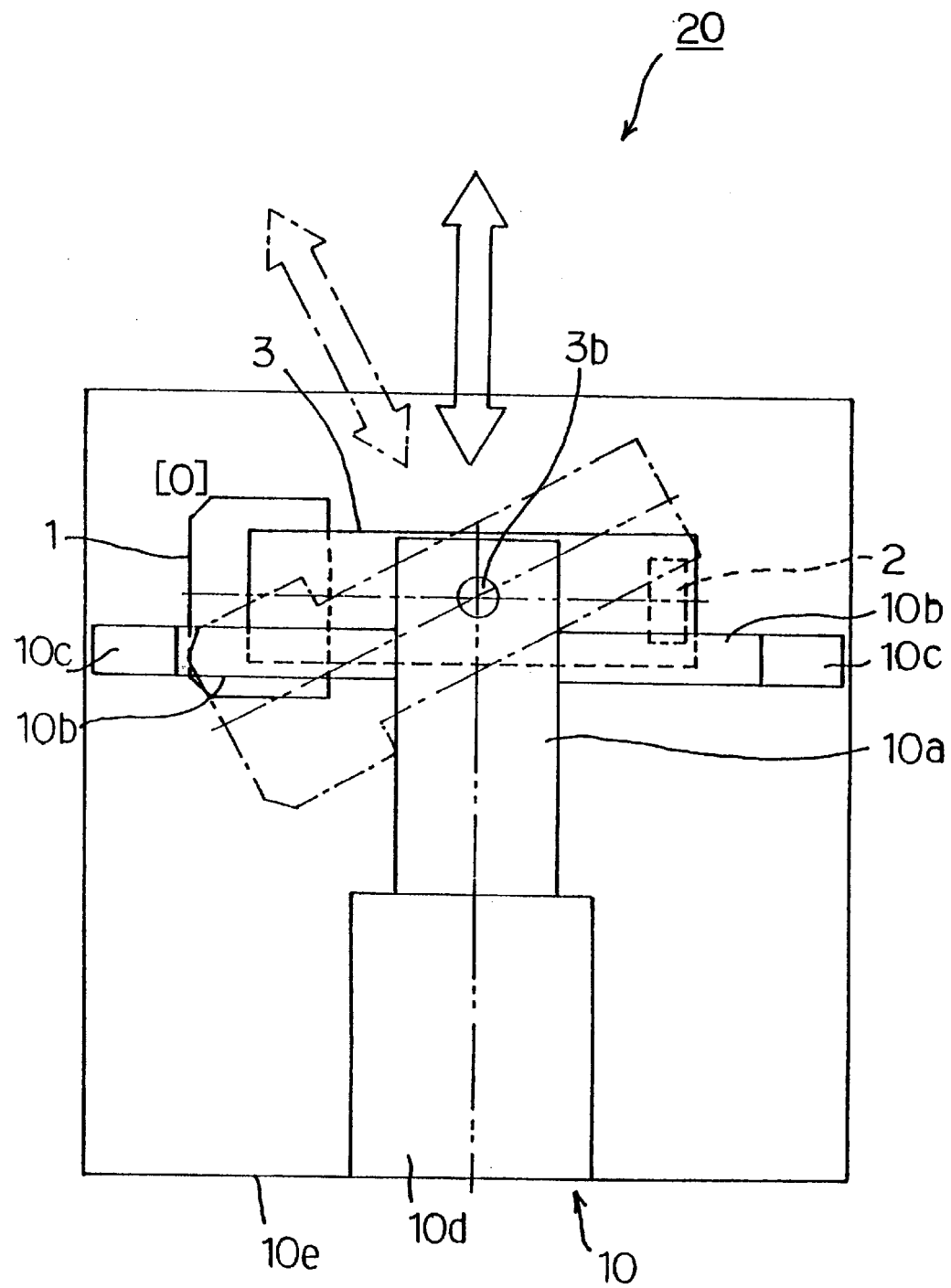
FIG. 23 is a plane view showing a standby position of a rotary arm according to the present invention.
Figure 24A:
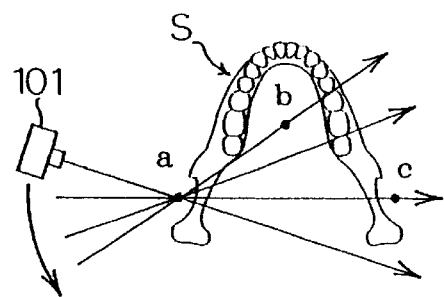
FIG. 24(a), FIG. 24(b), and FIG. 24(c) explain the operation of a rotary arm when a conventional X-ray panorama projection method is executed.
Figure 24B:
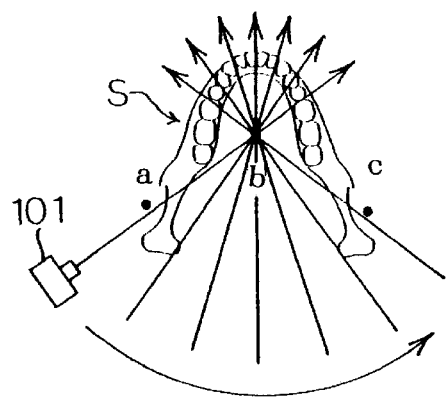
Figure 24C:
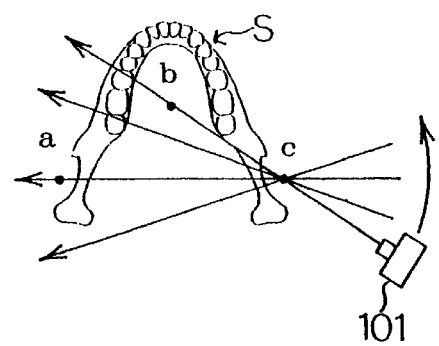
Figure 25:
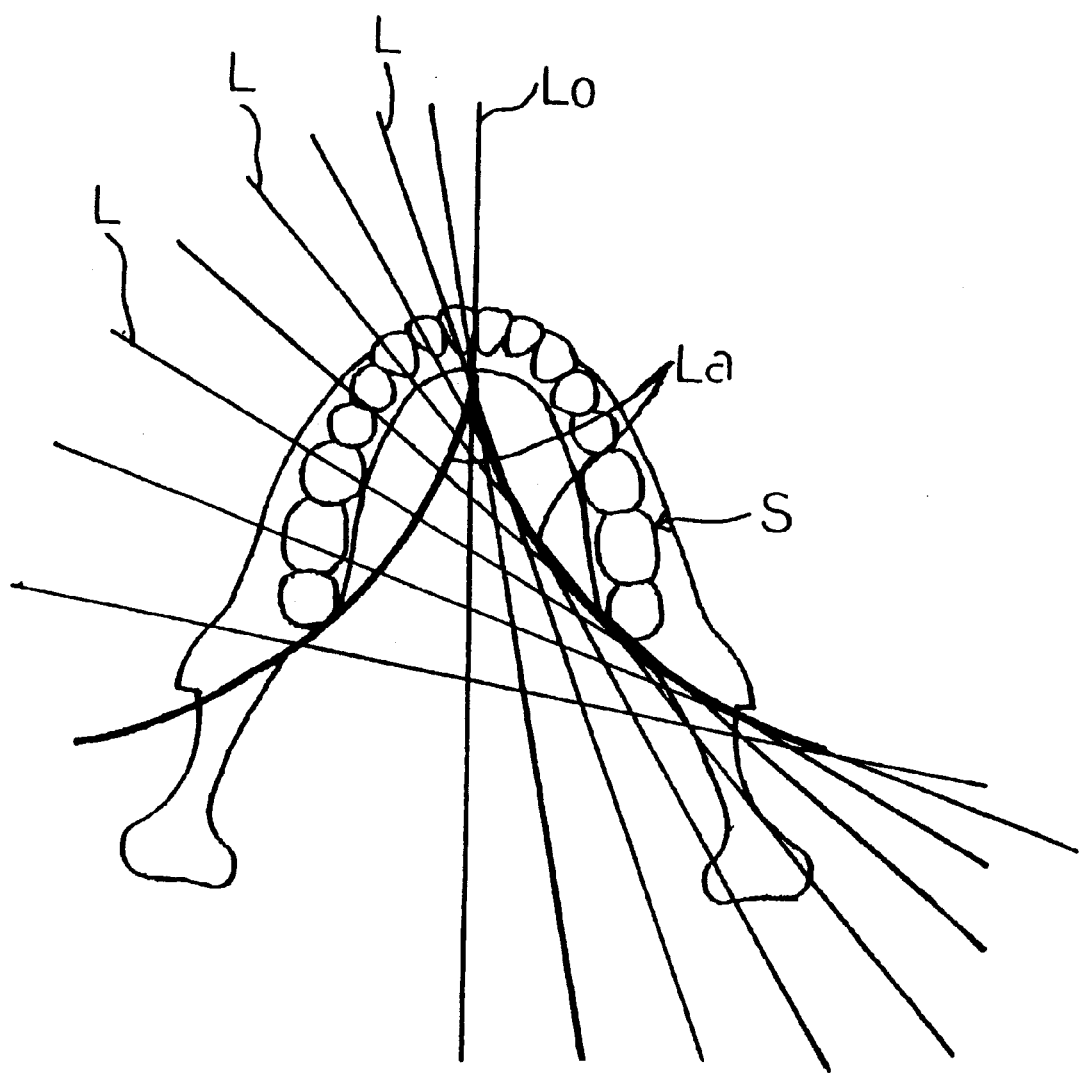
FIG. 25 illustrates operational excursion of a rotary arm of a conventional X-ray panorama projection system.

FIG. 23 is a plane view showing a standby position of the rotary arm according to the present invention.

The standby position [0] is set so that the patient enters or leaves under the rotary arm 3 of the system 20. In the figure, the rotary arm S is almost at right angle of the projected direction of the arm 10a of the main frame 10 at the standby position [0].

The standby position [0] is provided so that the patient who is the object O comes in and out the X-ray CT system 20 as shown in the outline arrow from upward of the figure. The rotary arm 3 is designed to wait ready at the standby position [0]. Therefore, the system 20 is convenient because the rotary arm 3 doesn't hinder the patient from coming in and out.

According to the installation site of the system 20, it is sometimes preferable to come in and out from other direction. In such a case, the stand-by position [0] of the figure can be positioned at substantially right angle against the access direction of the patient shown as a dashed line in the figure.

An embodiment of an X-ray CT method and system for a medical practice such as dental care is explained above, however, such a method and system can be used for not only a medical field but also a nondestructive test for detecting an alien object in a structure.

[Explanation of Fundamental Principle of X-ray CT Method]

Figure 26:
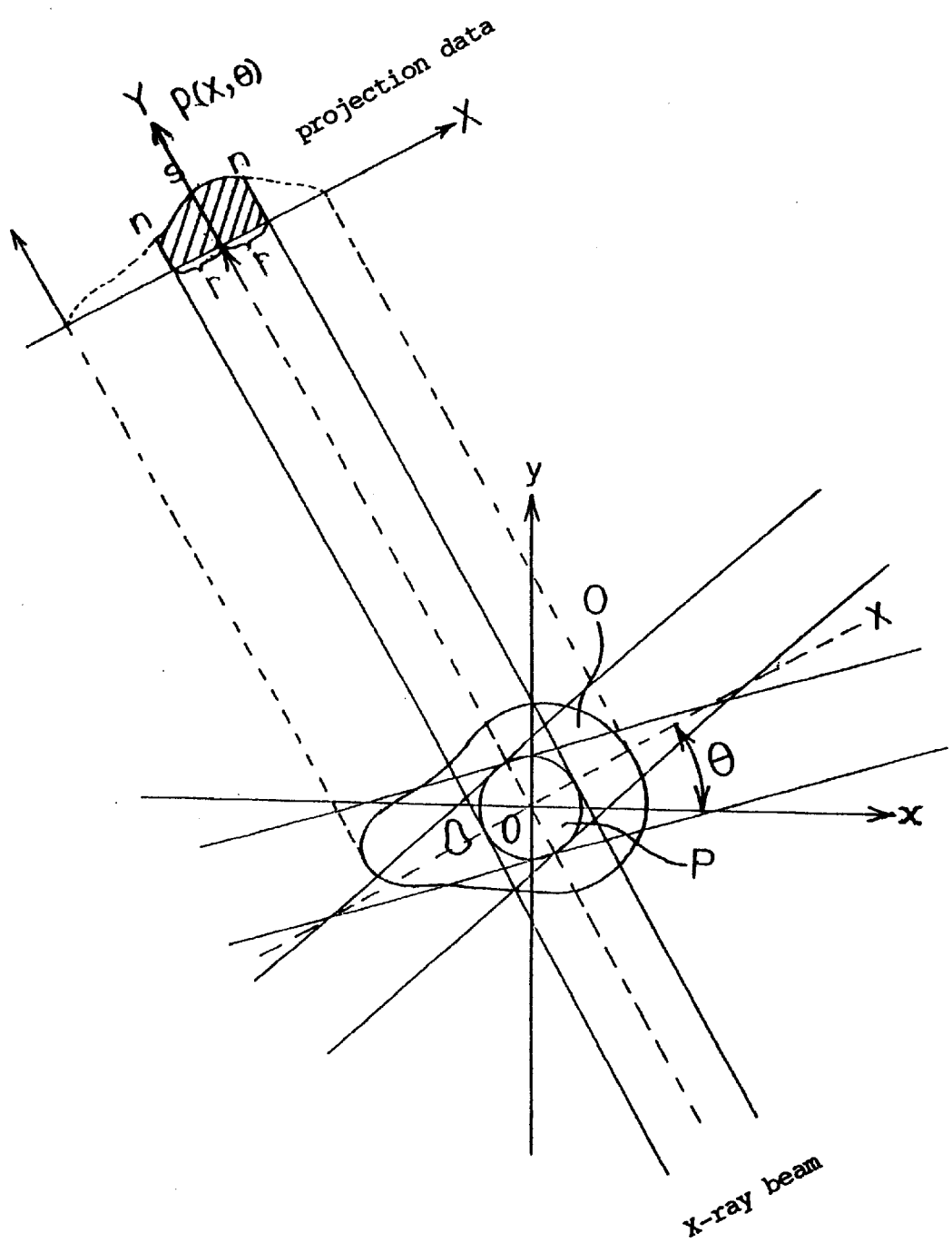
FIG. 26 illustrates a projection data of an X-ray CT method of the present invention.
Figure 30A:
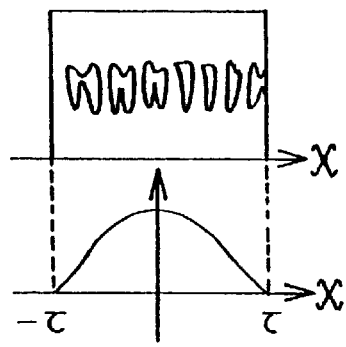
FIG. 30(a) and FIG. 30(b) explain an artifact measure for an X-ray CT method of the present invention.
Figure 30B:
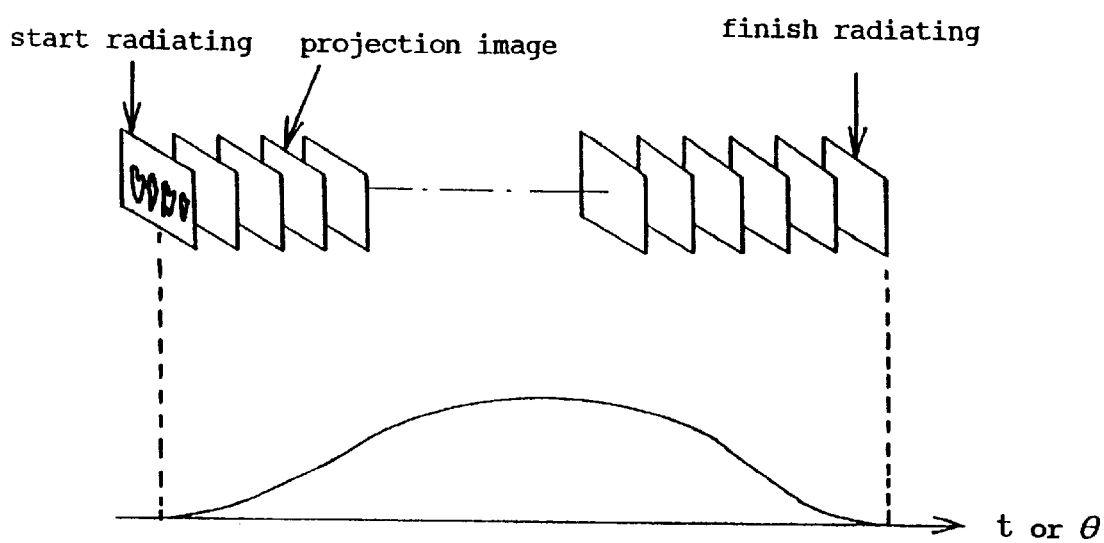
Figure 31:
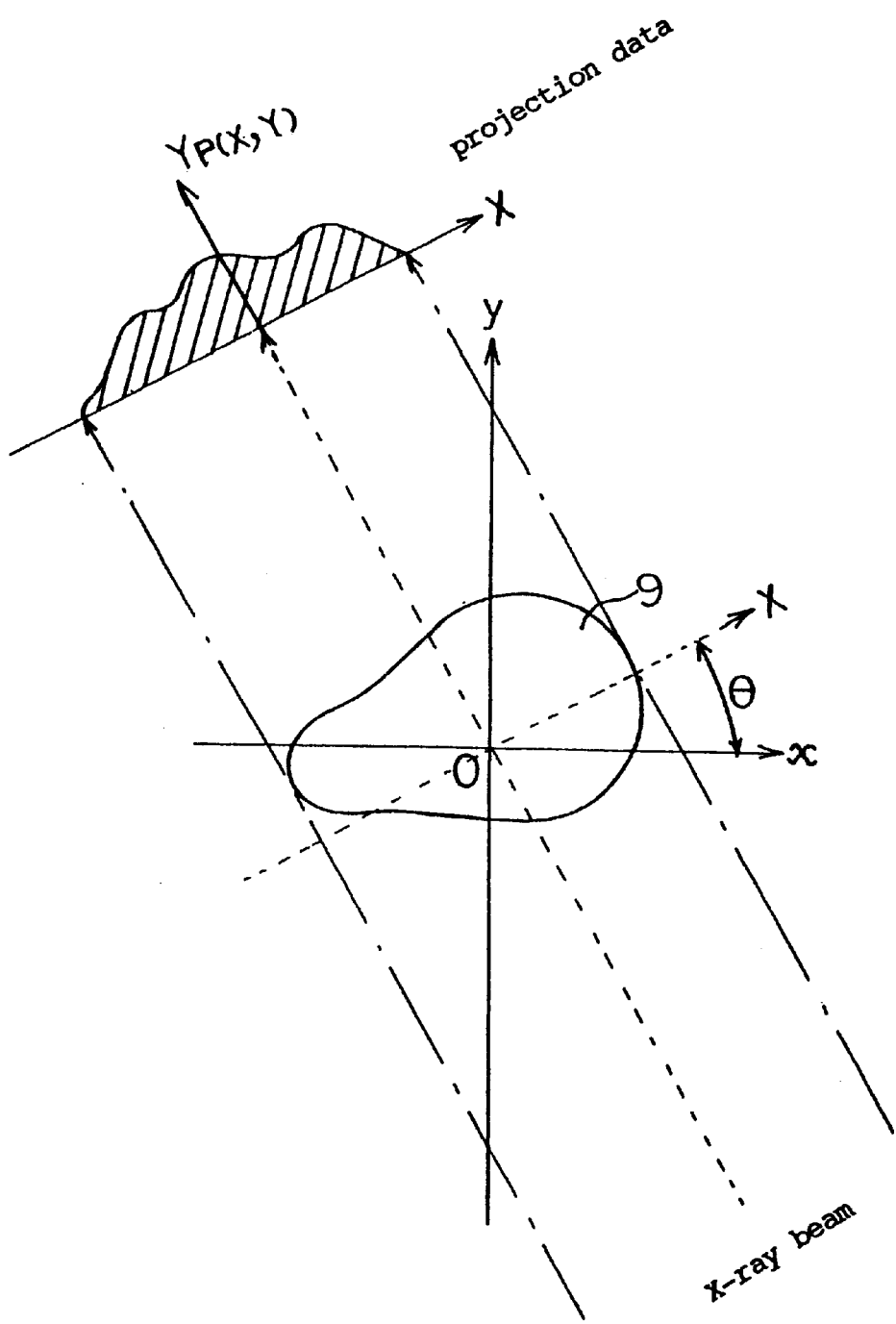
FIG. 31 shows a projection data analyzed by a conventional X-ray CT.

FIG. 26 explains a projection data of the ortho X-ray CT method of the present invention. FIG. 27(a), FIG. 27(b), and FIG. 27(c) explain conditional functions used in the ortho X-ray CT method of the present invention. FIG. 28(a), FIG. 28(b), FIG. 29(a), and FIG. 29(b) explain the fundamental principle of the X-ray CT method for producing a panorama image according to the present invention. FIG. 30(a) and FIG. 30(b) explain an artifact measure of the X-ray CT method of the present invention. FIG. 31 explains a projection data analyzed by a conventional X-ray CT. FIG. 32 shows conditional expressions used for a conventional X-ray CT method. FIG. 33 shows conditional expressions used for the X-ray CT method of the present invention. FIG. 34 shows conditional expressions used for the X-ray CT method for producing a panorama image according to the present invention. From these figures an X-ray CT method using a conical X-ray beam will be considered.

[Conventional X-ray CT Method]

When an object O is positioned on an x, y coordinate system, an X-ray beam is irradiated on all around the object O from an inclined angle θ, and a projection data is generated on an XY coordinate system (FIG. 31), the projection data is shown as a (formula 1) of FIG. 32 and the backprojected data is shown as a (formula 2) of FIG. 32 by the convolution method. It has been well known in the conventional analysis method.

A fixed coordinate system xOy is defined on a flat surface including the sectional image of the object O, the two-dimensional distribution information of the X-ray absorption coefficient at the coordinate (x, y) is expressed as an original image in the form of a continuous two-dimensional function f A parallel X-ray beam is irradiated from every angle direction θ, $0<θ<π$, and the intensity of the X-ray passed out of the object O is detected as a projection data.

In this case, as the two-dimensional distribution information f (x, y) of the absorption coefficient in the object O passed an X-ray beam can be obtained by the (formula 3), the integration is calculated and repeated at z-axis direction, namely vertical direction, so that the three-dimensional X-ray absorption coefficient distribution information of the object can be obtained.

The operation called as a data reconstruction by CT includes a two-dimensional Fourier transform method, one and two dimensional Fourier transform method, one dimensional Fourier transform method, and a convolution method. The above-mentioned convolution method is widely adapted these days to cut operation time drastically. According to the convolution method, only a convolution integral which is a simple sum of products and the backprojection operation are executed so that the calculation can be executed simply and at high speed.

According to the (formula 4) of FIG. 32, f (x, y) is obtained by a convolution method. The coordinate transformation formula in FIG. 32 is a transformation formula between x, y coordinate of the xOy coordinate and X, Y coordinate of an XOY coordinate.

[Normal X-ray CT Method of the Present Invention]

Figure 27:
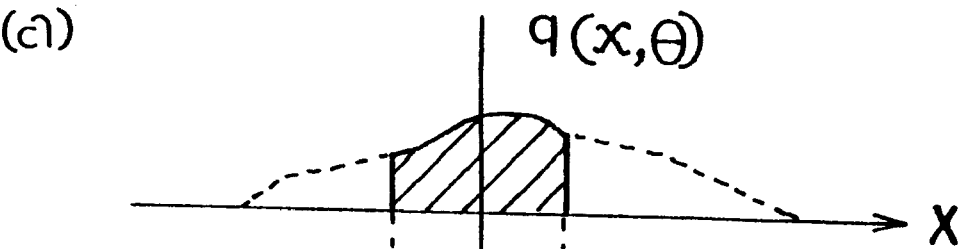
FIG. 27 illustrates conditional functions used in an X-ray CT method of the present invention.
Figure 27:
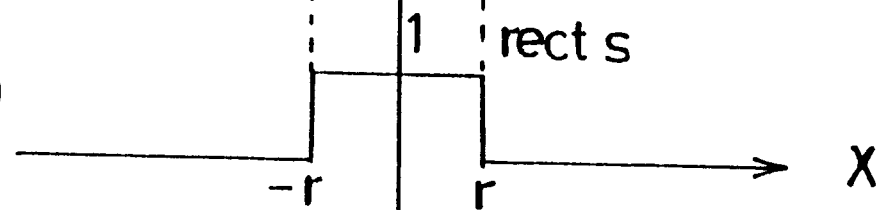
Figure 27:
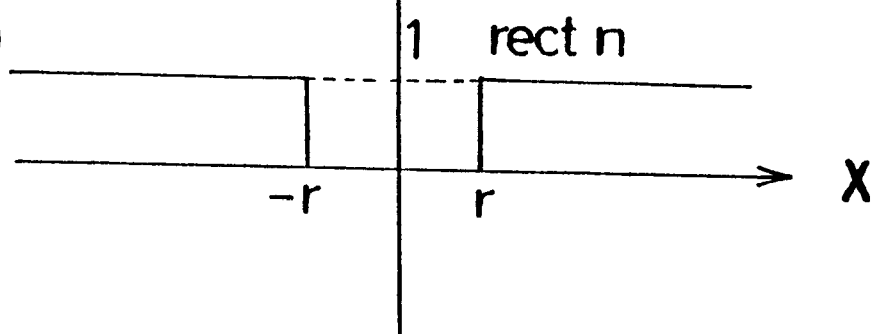

According to the normal X-ray CT method of the present invention, comparing to the conventional method, the conical X-ray beam is locally irradiated only on the local region P of the object O as shown in FIG. 26, and its radiant beam width 2r is shown in FIG. 27 and the conditional function as shown in (formula 5) of FIG. 33 is used.

When the conditional function (formula 5) is used, the relation of the (formula 6) in FIG. 33 is formed between the relation of a backprojection data qs (X, θ) of the local region P of the object, a backprojection data qn(X,θ) other than the local region P of the object O and a whole backprojection data q(X,θ) of the object O. In (formula 6-1) the second term becomes about [0] almost all the area between the interval [−r, r]

Namely, the whole projection data of the object O equals to the integration of the projection data of the local region P and the projection data passing through the other area which is an anteroposterior passage of the local region P, so that the relation; q(X,θ)=qs(X,θ)+qn(X,θ) . . . FIG. 33 (formula 7); is formed between each backprojection data and as a result (formula 8) in FIG. 33 is derived.

Therefore, the two-dimensional distribution information fs(x, y) of the X-ray absorption coefficient of the local region P can be obtained when the two-dimensional distribution information fn(x, y) of the X-ray absorption coefficient other than the local region P is subtracted from the two-dimensional distribution information f(x, y) of the X-ray absorption coefficient of the whole object O.

According to the characteristic of the present invention, comparing to the conventional X-ray CT method using a conical X-ray beam, the beam width in rotary direction of the conical X-ray beam is further minimized than the conventional beam width for radiating the whole object and only the local region which is a part of the object of the conical X-ray beam is irradiated. Such an idea can change the conventional idea wherein X-ray beam is irradiated on the whole object for X-ray CT projection.

The present projection method is based on the idea that the projection data can be always obtained from the local region irradiated by the conical X-ray beam, but the conical X-ray beam temporarily passes out the other area of the object around the local region according to rotation comparing to the local region so that the projection data isn't affected, and in case of backprojection, affect on the projection data other than the local region can be almost ignored. The above-mentioned conditional function (formula 5) expresses such an idea as a formula.

In other words, the two-dimensional distribution information fn(x, y) is an error element and indicates a signal of a rectn function outside of a rects function. While studying the present invention, the inventors of the present invention have found that the two-dimensional distribution information fn(x, y) indicating the error element becomes almost [0]. Accordingly, in the present invention, the error element can be almost disregarded and an image reconstruction can be clearly produced only at a desired local reagion P.

In case of applying dental projection, the main point is to analyze the shape of a tooth or an implanted tooth as a diagnosis object. Such parts have higher X-ray absorption coefficient than the other tissue, therefore, the two-dimensional distribution information fs(x, y) of the X-ray absorption coefficient of such a part becomes larger than the two-dimensional distribution information fn(x, y) of the X-ray absorption coefficient of the other tissue. Consequently more clear sectional image can be produced.

[X-ray CT Method for Producing Panorama Image of the Present Invention]

Next, the ortho X-ray CT method for producing a panorama image according to the present invention will be studied.

As mentioned above, according to the X-ray CT method of the present invention, it is characterized in that only the local region of the object is locally projected and the sectional image of the local region is obtained. In the present invention, this method is skillfully utilized to produce the panorama image of the dental arch which has been in heavily used in dental surgery.

Conventionally the dental arch should be irradiated while transferring the rotary center of the X-ray beam bundle so that the X-ray beam bundle draws a complicated excursion according to the panorama image condition in order to produce a panorama image. On the other hand, in the X-ray CT, the conical X-ray beam is rotated with the rotary center fixed at a predetermined position. Therefore, it has been a problem how to obtain a panorama image by utilizing the system only by achieving rotation with its center fixed, as it is.

In the CT wherein an fan shaped X-ray is irradiated on the dental arch from 360° all around and the rotary center is fixed at one position during projection, it has been known that only the X-ray projection data of the dental arch is extracted and reconstructed. However in this method, because the X-ray exposed dose has been large and the imaging system has been large-sized, such a problem has been desired to be solved.

According to the X-ray CT for producing a panorama image according to the present invention, in order to produce a panorama image of the dental arch, a virtual local region is calculated so as to always pass the conical X-ray beam irradiated by a fixed excursion which has been required to produce a panorama image conventionally. The conical X-ray beam is locally irradiated so as to include only the virtual local region while fixing the rotary center of the conical X-ray beam at the center of the virtual local region and only the partial X-ray projection image by the conical X-ray beam is extracted from the obtained X-ray projection image of the dental arch. Based on the partial X-ray projection image, backprojection is executed to obtain the three-dimensional absorption coefficient distribution information and the panorama image of the dental arch is produced by the obtained three-dimensional absorption coefficient distribution information.

Accordingly, the panorama image of the dental arch using the conical X-ray beam like conventional one can be obtained using the X-ray CT method.

This basic idea is a developed one from the X-ray CT method for irradiating a conical X-ray beam on the whole object down to the X-ray CT method. When the virtual local region is selected as above mentioned, the locally projected conical X-ray beam is limitedly radiated on only a prescribed angle area of the dental arch for obtaining a panorama image. Adequate image data for a panorama image can be obtained by extracting the partial X-ray projection image only on the irradiated angle area of the conical X-ray beam. The absorption coefficient distribution information is obtained from the partial projection image data and a panorama image is produced.

The virtual local region to obtain the panorama image of the dental arch is located around the center of the dental arch, namely at the axis of symmetry of the dental arch and also an appropriate position between the cervical vertebrae and the dental arch. Such an area is advantageous because it has little obstacle.

The formulas used for the X-ray CT for producing a panorama image are almost the same, however, a little consideration is required for an integration range, a filter function for backprojection, and a filter function used for an X-ray projection data.

Figure 28A:
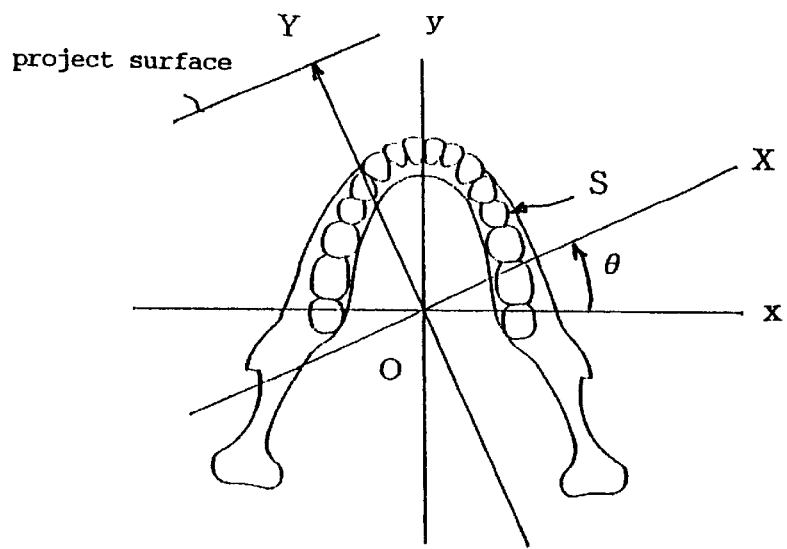
FIG. 28(a) and FIG. 28(b) explains the fundamental principle of an X-ray CT method for producing a panorama image according to the present invention.

According to the method, the center of xOy coordinate and XOY coordinate become the center of the virtual local region and become the center of the dental arch when an orthodox projected panorama image of the dental arch is produced. Here such an example is explained. FIG. 28(a) explains such a projection method and FIG. 28(b) explains an integration range.

The (formula 9) and (formula 10) in FIG. 34 used in this method are the same as the (formula 5) and (formula 6) in FIG. 33 for the above-mentioned X-ray CT method. However, the value of "2r" is the beam width in rotary direction of a conical X-ray beam, not a conical X-ray beam.

The qs(X,θ) is a backprojection data from the partial X-ray projection image data by an actually projected conical X-ray beam. The qn(X,θ) is a backprojection data from the X-ray projection image data by the X-ray beam bundle which hasn't been actually radiated but exists in the conventional X-ray CT method.

According to the method, because the irradiation area of the conical X-ray beam is limited, only qs(X,θ) relating to rects(X) is actually obtained, thereby qn(X,θ)=0. Therefore, backprojection is executed using qs(X,θ) and (formula 11) is derived from (formula 10).

According to a normal ortho X-ray CT method of the present invention, the integration range of θ is [0, 2π] or [0,π] when fs(x, y) is obtained. The integration range is further limited in this method.

Figure 28B:
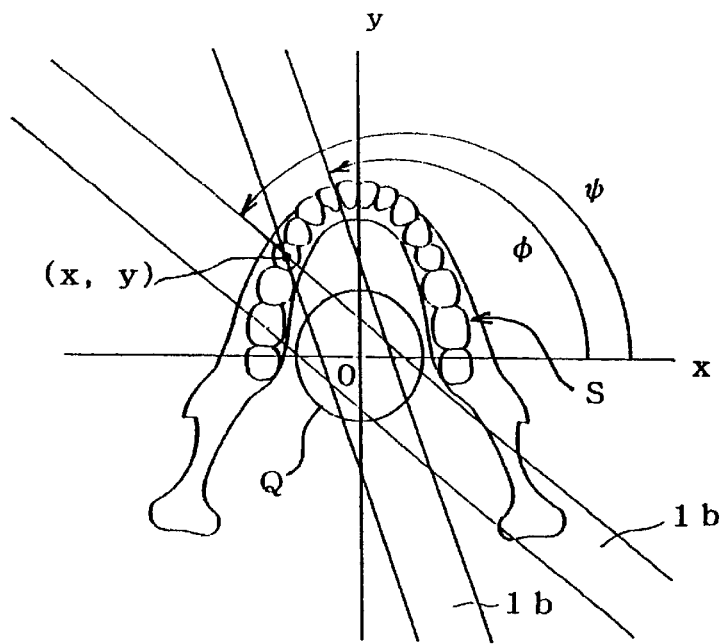

FIG. 28(b) shows the integration range. As shown the figure, the integration range of this method is, when the point (x, y) of the dental arch S is considered, from the angleφ (x, y) starting projection of the conical X-ray beam on the point (x, y) to the angleψ(x, y) finishing projection.

The meaning of starting and finishing is that they are design value for calculation and the value smaller than the angle which the conical X-ray beam actually irradiates the point (x, y), namely an optional integration range from the angle φ(x, y) to the angle ψ(x, y), can be selected. Because the angle φ(x, y) and the angle ψ(x, y) can be determined as design values at an optional point of the dental arch, they become the function of x and y.

Using the angle φ(x, y) and the angle ψ(x, y), the backprojection formula of the present invention is shown in (formula 12) in FIG. 32.

Figure 29A:
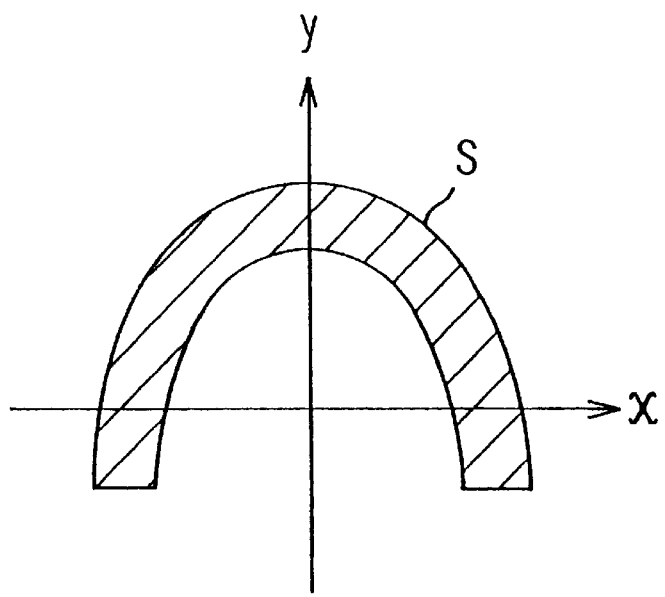
FIG. 29(a) and FIG. 29(b) explain the fundamental principle of an X-ray CT method for producing a panorama image according to the present invention.
Figure 29B:
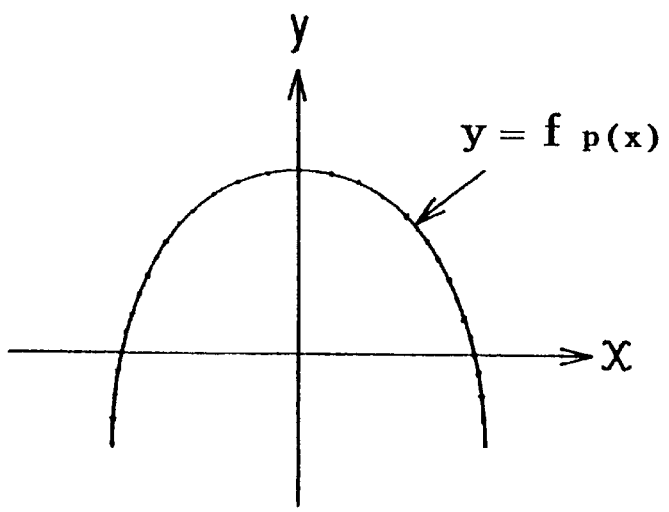

The range for calculating fs(x, y) of the (formula 12) may be the required range of the dental arch S shown in FIG. 29(a). The sectional image of the dental arch represented by the formula, y=fp(x), is determined in advance as shown in FIG. 29(b) and fs(x, y) of the (formula 12) may be calculated only about the point (x, fp(x)) on the surface.

[Artifact Measure]

Next an artifact measure caused by operating the fs(x, y) will be described. The artifact is, also called a false image, a discordance of data produced where the values of the conditional expressions are rapidly changed in image processing. Following artifact measure may be taken in order to eliminate such an artifact.

<Artifact Measure 1>

As the terminal of the above-mentioned conditional functions rects(X) is rapidly changed from 0 to 1, an artifact is apt to be caused at the point on the beam passing the point (x, y) at the finishing angle φ(x, y) and the angleψ(x, y) at which the conical X-ray beam starts or finishes radiating. The filter function changing more smoothly at the terminal is preferably used for calculating the (formula 10) instead of rects(X) to eliminate the artifact.

Following Hamming function, Hanning function or Blackman function may be used for the filter function.

Hamming function: Hamming (τ, X)=0.54−0.46*cos(2π*X/2τ)

Hanning function: Hanning (τ, X)=0.5*(1.0−cos(2π*X/2τ)

Blackman function: Blackman (τ, X)=0.42−0.5*cos(2π*X/2τ)+0.08*COS(4π*X/2τ)

These functions are used for excluding the artifact at both terminals at the relation in FIG. 30(a).

The functions aren't limited in the above-mentioned and any function of which terminals smoothly approach [0] may be used.

In the above formula, "*" indicates multiplication.

<Artifact Measure 2>

Another artifact element which is generated at starting and finishing of the conical X-ray beam irradiation as shown in FIG. 30(b) can be considered. The filter function the same as the above artifact measure 1 can be used for such an element.

What is claimed is:

1. An X-ray computed tomography method of the local region of the object in which X-rays are radiated locally on part of the object, by turning a rotary arm with an X-ray generator and a two-dimensional image sensor faced to each other, the method comprising:

producing an X-ray projection image of a local region on the two-dimensional X-ray image sensor by turning the rotary arm within a scope of angle according to projection conditions, while locally radiating conical X-ray beams from the X-ray generator covering only the local region of the object, with a rotating center of the rotary arm fixed at a center position of the local region, the local region being a part of the object to be examined, and arithmetically processing the X-ray projection image thus produced and extracting a three-dimensional X-ray absorption coefficient distribution information on the local region and thereby producing a sectional image of the local region of the object to be examined.

2. An X-ray computed tomography method according to claim 1, wherein the X-ray projection image of the local region is formed by using a conical X-ray beam defined as 2r in width in rotating direction of the beam from the X-ray generator, and wherein a two-dimensional distribution information fs(x, y) of the X-ray absorption coefficient of the local region is calculated by using the following equations when extracting the three-dimensional X-ray absorption coefficient distribution information on the local region as image information:

$$X = x\cos\theta + y\sin\theta, \ Y = -x\sin\theta + y\cos\theta$$

$$p(X, \theta) = \int f(x, y)dY \text{ wherein integration scope: } [-\infty, \infty]$$

-continued $$q(X, \theta) = (1/2) \int \{rects(X') + rectn(X')\} p(X', \theta) h(X - X') dX'$$

wherein integration scope: $[-\infty, \infty]$ $$= (1/2) \int rects(X') p(X', \theta) h(X - X') dX' +$$

$$(1/2) \int rectn(X') p(X', \theta) h(X - X') dX'$$

wherein integration scope: $[-\infty, \infty]$ $$= qs(X, \theta) + qn(X, \theta)$$

$$f(X, y) = (1/2\pi) \int \{qs(X, \theta) + qn(X, \theta)\} d\theta$$

wherein integration scope: $[0, 2\pi]$ $$= fs(x, y) + fn(x, y)$$

$$fs(x, y) = f(x, y) - fn(x, y)$$

wherein $r * r \geq X * X + y * y$ in which:
- x, y are coordinates x, y on an x, y coordinate system set and fixed on the plane over which a horizontal conical X-ray beam from the X-ray generator passes with a center of the local region of the object as origin,
- X, Y are coordinates X, Y on an X, Y coordinate system defined in relation to turning of the conical X-ray beam where X, Y coordinate system has the same origin that of the x, y coordinate system and has turned relation with respect to the fixed x, y coordinate system on the same plane,
- θ is a gradient of the X, Y coordinate system in relation to the x, y coordinate system,
- X' is a variable of the coordinate X to obtain a backprojection data in relation to a point (X, θ) in the X, Y coordinate system,
- rects and rectn are conditional functions of the conical X-ray beam which is defined from the following values:
  - If $|X| \leq r$, then rects (X)=1
  - If $|X| > r$, then rects (X)=0
  - If $|X| \leq r$, then rectn (X)=0
  - If $|X| > r$, then rectn (X)=1
  - rects (X)+rectn (X)=1 wherein any of those equations is applicable when the conical X-ray beam is radiated on the local region of the object,
- f(x, y) is a two-dimensional distribution information of the X-ray absorption coefficient when the X-ray is radiated on the whole object,
- fs(x, y) is a two-dimensional distribution information on the X-ray absorption coefficient on the x, y coordinate system when the X-ray is locally radiated only on the local region of the object,
- fn(x, y) is a two-dimensional distribution information of the X-ray absorption coefficient on the x, y coordinate system when the X-ray is locally radiated only on other than the local region of the object,
- p(X, θ) is a whole projection data on the X, Y coordinate system,
- q(X, θ) is a whole backprojection data on the object on the X, Y coordinate system,
- qs (X, θ) is a backprojection data on the X, Y coordinate system when the X-ray is locally radiated only on the local region of the object,
- qn(X, θ) is a backprojection data on the X, Y coordinate system when the X-ray is radiated only on other than the local region of the object, and
- the symbol ∫ indicates integration, the letters "s", and "n" in rects, rectn, qs, qn, fs and fn are suffixes and the symbol * (used only when necessary) indicates multiplication.

3. An X-ray computed tomography method in which X-rays are radiated locally on part of an object by turning a rotary arm with an X-ray generator and a two-dimensional image sensor faced to each other, the method comprising:

successively producing X-ray projection images of a dental arch on the two-dimensional X-ray image sensor by radiating a conical X-ray beam covering only a virtual local region from the X-ray generator while turning the rotary arm within a scope of angle according to projection conditions with a rotating center of the rotary arm fixed at a center position of such a virtual local region as containing an orbit of the conical X-ray beam required to obtain a panoramic image of the dental arch, or part of the object, and taking out only partial X-ray projection images produced by the conical X-ray beam out of the X-ray projection images of the dental arch successively formed on the two-dimensional image sensor and then arithmetically processing the X-ray projection images thus picked out so as to extract a three-dimensional X-ray absorption coefficient distribution information on the dental arch as image information and thereby producing a panoramic image of the dental arch.

4. An X-ray computed tomography method according to claim 3, wherein the partial X-ray projection image is formed by using a conical X-ray beam defined as 2r in width in a rotating direction of the beam from the X-ray generator, and wherein a two-dimensional distribution information fs (x, y) of the X-ray absorption coefficient of the dental arch is calculated by using the following equations when extracting the three-dimensional X-ray absorption coefficient distribution information on the dental arch as image information:

$$X = x\cos\theta + y\sin\theta, \ Y = -x\sin\theta + y\cos\theta$$

$$p(X, \theta) = \int f(x, y) dY \text{ wherein integration scope: } [-\infty, \infty]$$

$$q(X, \theta) = (1/2) \int \{rects(X') + rectn(X')\} p(X', \theta) h(X - X') dX'$$

wherein integration scope: $[-\infty, \infty]$ $$= (1/2) \int rects(X') p(X', \theta) h(X - X') dX' +$$

$$(1/2) \int rectn(X') p(X', \theta) h(X - X') dX'$$

wherein integration scope: $[-\infty, \infty]$ $$= qs(X, \theta) + qn(X, \theta)$$

$$= qs(X, \theta) \quad \because qn(X, \theta) \approx 0$$

$$fs(x, y) = (1/(\psi(x, y) = \phi(x, y))) \int \{qs(X, \theta)\} d\theta$$

wherein integration scope: $[\phi(x, y), \psi(x, y)]$ in which:
- x, y are coordinates x, y on an x, y coordinate system set and fixed on the plane over which a horizontal conical X-ray beam from the X-ray generator passes with a center position of a virtual local region as origin, X, Y are coordinates X, Y on an X, Y coordinate system defined in relation to turning of the conical X-ray beam where the X, Y coordinate system has the same origin that of the x, y coordinate system and has turned relation with respect to the fixed x,y coordinate system on the same plane, θ is a gradient of the X, Y coordinate system in relation to the x, y coordinate system, φ(x, y) is a radiation angle at which radiation of a conical X-ray beam begins on a point of the dental arch (x, y), or a value of the angle θ, ψ(x, y) is a radiation angle at which radiation of the conical X-ray beam ends on the point of the dental arch (x, y), or the value of the angle θ, X' is a variable of the coordinate X to obtain a back-projection data in relation to a point (X, θ) in the X, Y coordinate system, rects and rectn are conditional functions of the conical X-ray beam which is defined by the following values:

If $|X| \leq r$, then rects (X)=1

If $|X| > r$, then rects (X)=0

If $|X| \leq r$, then rectn (X)=0

If $|X| > r$, then rectn (X)=1 rects (X)+rectn (X)=1 wherein any of those equations is applicable when the conical X-ray beam is radiated on the virtual local region of the object to gain the X-ray projection image extracted by using the conical X-ray beam, f(x, y) is a two-dimensional distribution information of the X-ray absorption coefficient when the X-ray is radiated on the whole object, fs(x, y) is a two-dimensional distribution information of the X-ray absorption coefficient on the x, y coordinate system when the X-ray is locally radiated only on the virtual local region of the object, fn(x, y) is a two-dimensional distribution information of the X-ray absorption coefficient on the x, y coordinate system when the X-ray is locally radiated only on other than the virtual local region of the object, p(X, θ) is a whole projection data on the X, Y coordinate system, q(X, θ) is a whole backprojection data on the object on the X, Y coordinate system, qs (X, θ) is a backprojection data on the X, Y coordinate system when an X-ray is locally radiated only on the virtual local region of the object, qn (X, θ) is a backprojection data on the X, Y coordinate system when the X-ray is radiated only on other than the vitual local region of the object, and the symbol ∫ indicates integration, the letters "s" and "n" in rects, rectn, qs, qn, fs and fn are suffixes.

5. The X-ray computed tomography method according to claim 3, wherein the X-ray generator is designed such that only the conical X-ray beam is selectively radiated on the virtual local region out of the conical X-ray beam radiated from the X-ray generator in synchronism with rotation of the rotary arm during projection, thereby producing a partial X-ray projection image of the dental arch on the two-dimensional X-ray image sensor.

6. The X-ray computed tomography method according to claim 5, wherein only the conical X-ray beam is selectively radiated by moving a slit in an X-ray scanning direction in front of the X-ray generator during projection.

7. An X-ray computed tomography system comprising:

an X-raying means having a rotary arm with an X-ray generator and a two-dimensional X-ray image sensor faced to each other, an X-ray beam width restriction means for restricting a width of a conical X-ray beam radiated from the X-ray generator at least in a scanning direction, a rotary arm drive control means for rotating the rotary arm with a rotation center of the rotary arm fixed during projection, the means being so designed to move and preset at least one of a rotation center of the rotary arm and an object to be X-rayed before projection, and an image processing unit for arithmetically processing an X-ray projection data and extracting a three-dimensional absorption coefficient distribution information of the object through which the X-ray is passed as image information, wherein the rotary arm is turned in order to form an X-ray projection image of the two-dimensional image sensor within a scope of angle according to projecting conditions, while controlling a beam width of the conical X-ray beam from the X-ray generator which contain a local region of the object, or a part of the object and widens in X-ray scanning direction and the X-ray projection image thus formed is arithmetically processed to produce a sectional image of the local region of the object.

8. An X-ray computed tomography system comprising:

an X-raying means having a rotary arm with an X-ray generator and a two-dimensional X-ray image sensor faced to each other, an X-ray beam width restriction means for restricting a width of a conical X-ray beam radiated from the X-ray generator at least in a scanning direction, a rotary arm drive control means for rotating the rotary arm, and an image processing unit for arithmetically processing an X-ray projection data and extracting a three-dimensional absorption coefficient distribution information of an object through which the X-ray is passed as image information, wherein the conical X-ray beam containing only a virtual local region is radiated from the X-ray generator so as to successively form an X-ray projection image of a dental arch on the two-dimensional sensor, while turning the rotary arm within a scope of angle according to pojecting conditions, with a center of the rotary arm fixed at a center of the virtual local region containing an orbit of the conical X-ray beam required to obtain a panoramic image of the dental arch, or a part of the object, and only partial X-ray projection image of the dental arch formed by radiation of the conical X-ray beam is taken out of the X-ray projection image of the dental arch successively formed on the two-dimensional sensor and then the partial X-ray projection image of the dental arch is arithmetically processed so as to extract the three-dimensional absorption coefficient distribution information of the dental arch as image information and thereby producing a panorama image of the dental arch.

9. The X-ray computed tomography system according to claim 8, wherein the X-ray generator is provided with an radiation control slit for selectively permitting emission of only the conical X-ray beam out of a specific width of conical X-ray beam from the X-ray generator synchronizing with rotation of the rotary arm and wherein the partial X-ray projection images of the dental arch are formed on the two-dimensional image sensor by emission of the conical X-ray beam through the radiation control slit.

10. The X-ray computed tomography system according to claim 8, wherein the X-ray generator is provided with an radiation control slit for selectively permitting of emission of only the conical X-ray beam out of a specific width of the conical X-ray beam from the X-ray generator by moving the slit in front of the X-ray generator in an X-ray scanning direction, synchronizing with rotation of the rotary arm during projection and wherein the partial X-ray projection images of the dental arch are formed on the two-dimensional image sensor by emission of the conical X-ray beam through the radiation control slit.

11. An X-ray computed tomography system comprising:
  an X-raying means having a rotary arm with an X-ray generator and a two-dimensional X-ray image sensor faced to each other,
  an X-ray beam width restriction means for restricting a width of a conical X-ray beam radiated from the X-ray generator at least in a scanning direction,
  a rotary arm drive control means for rotating the rotary arm with a rotation center of the rotary arm fixed during projection, the means being so designed to move and preset one of a rotation center of the rotary arm and an object to be X-rayed before projection, and
  an image processing unit for arithmetically processing an X-ray projection data and extracting a three-dimensional absorption coefficient distribution information of the object through which the X-ray is passed as image information,
  wherein the X-ray generator is further provided with a selection switch for selectively setting a local computed tomography mode where a sectional image of the local region is produced according to claim 7, or a panoramic radiographic mode where a panoramic image of the dental arch is produced according to claim 8.

12. An X-ray computed tomography system comprising:
  an X-raying means having a rotary arm with an X-ray generator and a two-dimensional X-ray image sensor faced to each other,
  an X-ray beam width restriction means for restricting a width of a conical X-ray beam radiated from the X-ray generator at least in the scanning direction,
  a rotary arm drive control means for rotating the rotary arm with a rotation center of the rotary arm fixed during projection, the means being so designed to move and preset one of the rotation center of the rotary arm and an object to be X-rayed before projection, and an image processing unit for arithmetically processing
  an X-ray projection data and taking out a three-dimensional absorption coefficient distribution information of the object through which the X-ray is passed as image information,
  wherein the X-ray generator is provided with a radiation control slit for permitting radiation of only the conical X-ray beam out of a specific width of the conical X-ray beam from the X-ray generator by moving the slit before the X-ray generator in an X-ray scanning direction synchronizing with a rotation of the rotary arm during projection through the slit, and wherein the system is further provided a selection switch for selectively setting a local computed tomography mode where a sectional image of the local region is produced according to claim 7 or a panoramic radiographic mode where a panoramic image of the dental arch is produced according to claim 9 or 10.

13. The X-ray computed tomography system according to one of claims 7 to 10, wherein the conical X-ray beam from the X-ray generator is horizontally radiated to the two-dimensional X-ray image sensor and wherein the rotating axis of the rotary arm is vertically provided.

14. The X-ray computed tomography system according to one of claims 7 to 10, wherein the two-dimensional X-ray image sensor has a detection face not longer than 30 cm in length and not longer than 30 cm in width and is capable of detecting more than 30 pieces of X-ray projection image data or partial X-ray projection image data per a second.

15. The X-ray computed tomography system according to one of claims 7 to 10, wherein the system is provided with a main frame for rotatably holding the rotary arm, the frame having an arm vertical position adjusting means for adjusting and setting the arm in a vertical direction.

16. The X-ray computed tomography system according to one of claims 7 to 10, wherein the system is provided with an object holding means for holding an object, the object holding means having an object horizontal position adjusting means for adjusting and setting the object in a horizontal direction.

17. The X-ray computed tomography system according to claim 16, wherein the object holding means is provided with an object vertical position adjusting means for adjusting and setting the object in a vertical direction.

18. The X-ray computed tomography system according to one of claims 7 to 10, wherein the system is provided with an optical beam radiation means for emitting optical beam so as to point out the rotation center of the rotary arm and a radiation axis of the conical X-ray beam.

19. The X-ray computed tomography system according to claim 7, wherein the system is further comprised of an object holding means which is so constructed as to movably secure a dental articulation model for setting the object thereon, the dental articulation model being previously made with respect to the object to be examined and positioning the rotation center of the rotary arm to the center of the local region of the object defined by the dental articulation model for an X-ray computed tomography, by moving the dental articulation model to the position on the object holding means pointed out by the optical beam from the optical beam radiation means by using the object horizontal position adjusting means or the object vertical position adjusting means provided on the object holding means.

20. The X-ray computed tomography system according to one of claims 8 to 10, wherein the system is further comprised of an object holding means which is so constructed as to movably secure a dental articulation model for setting the object thereon, the dental articulation model being previously made with respect to the object to be examined and positioning the rotation center of the rotary arm to the center of the virtual local region defined by the dental articulation model for a panorama X-raying computer tomography, by moving the dental articulation model to the position on the object holding means pointed out by the optical beam from the optical beam radiation means by using the object horizontal position adjusting means or the object vertical position adjusting means provided on the object holding means.

21. The X-ray computed tomography system according to one of claims 7 to 10, wherein the rotary arm drive control means is composed of a direct driven rotation control motor provided on the rotation center of the rotary arm.

22. The X-ray computed tomography system according to claim 21, wherein the rotary arm is formed with a hollow in the rotation center thereof.

23. The X-ray computed tomography system according to one of claims 7 to 10, wherein the two-dimensional X-ray image sensor is composed of either TFT, MOS, CCD, XII, or XICCD.

24. The X-ray computed tomography system according to one of claims 7 to 10, wherein the rotary arm is designed such that it moves to such a standby position as previously set as not stand in the way of the object to come in and go out when the object is set up for starting or finishing an X-ray computer tomography.

* * * * *